(12) United States Patent
Anderson et al.

(10) Patent No.: US 10,571,260 B2
(45) Date of Patent: Feb. 25, 2020

(54) AUTOMATED RIVET MEASUREMENT SYSTEM

(71) Applicant: The Boeing Company, Chicago, IL (US)

(72) Inventors: Patrick L. Anderson, Sammamish, WA (US); Stephen J. Bennison, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 261 days.

(21) Appl. No.: 15/697,442

(22) Filed: Sep. 6, 2017

(65) Prior Publication Data

US 2019/0072381 A1    Mar. 7, 2019

(51) Int. Cl.
| | |
|---|---|
| *G01B 11/27* | (2006.01) |
| *G06T 7/00* | (2017.01) |
| *G01N 21/95* | (2006.01) |

(52) U.S. Cl.
CPC ......... *G01B 11/27* (2013.01); *G01N 21/9515* (2013.01); *G06T 7/001* (2013.01); *G06T 2207/10116* (2013.01); *G06T 2207/30164* (2013.01)

(58) Field of Classification Search
None
See application file for complete search history.

(56) References Cited

U.S. PATENT DOCUMENTS

| | | |
|---|---|---|
| 5,768,409 A | 6/1998 | Csipkes et al. |
| 9,410,895 B2 | 8/2016 | Kilibarda et al. |
| 2015/0005945 A1 | 1/2015 | Toh |
| 2016/0082598 A1* | 3/2016 | Anducas Aregall ... B25J 19/022 382/153 |
| 2017/0056960 A1 | 3/2017 | Ficken et al. |
| 2018/0005362 A1* | 1/2018 | Wang ..................... G06K 9/036 |
| 2018/0009000 A1* | 1/2018 | Shang .................. H04N 13/204 |

OTHER PUBLICATIONS

Liu, Z., Ramuhalli, P., Safizadeh, S., & Forsyth, D. S. (2008). Combining multiple nondestructive inspection images with a generalized additive model. Measurement Science and Technology, 19(8), 085701. (Year: 2008).*
European Patent Office Communication and Extended Search Report, dated Feb. 13, 2019, regarding Application No. 18192191.7, 6 pages.

* cited by examiner

*Primary Examiner* — David Perlman
(74) *Attorney, Agent, or Firm* — Yee & Associates, P.C.

(57) ABSTRACT

An automated rivet measurement system comprises a number of end effectors, a number of cameras, a processor, and a comparator. The number of end effectors is configured to perform drilling and riveting on a structure. The number of cameras is connected to the number of end effectors. The number of cameras is configured to take a first image of a hole in the structure and a second image of a rivet in the hole. The processor is configured to process the first image and the second image to identify a number of reference points in the first image and the second image. The comparator is configured to determine a rivet concentricity using the hole in the first image and the rivet in the second image, in which the first image and the second image are aligned using the number of reference points.

25 Claims, 15 Drawing Sheets

AUTOMATED RIVET MEASUREMENT SYSTEM

BACKGROUND INFORMATION

1. Field

The present disclosure relates generally to manufacturing vehicles, and in particular, to installing fasteners in vehicles using a rivet measurement system. Still more particularly, the present disclosure relates to an automated rivet measurement system configured to install rivets and determine rivet concentricity.

2. Background

In manufacturing vehicles, fasteners are installed to connect parts to each other. For example, hundreds of thousands or more rivets may be installed in a commercial aircraft. Inspection of the installed rivets is performed to determine whether the rivets meet specifications for the commercial aircraft.

The inspection may be performed in a number of different ways. The inspections may be performed using non-destructive testing and destructive testing.

Non-destructive testing may be performed by having human operators make measurements with tools, such as gauges or probes. Additionally, non-destructive testing may be performed using robots that have an end effector configured to make measurements. Measurements of rivets also may be obtained using cameras or laser measurement tools.

Some measurements, however, may not be easily made using human operators or robots with gauges, probes, cameras, or laser measurement tools. For example, some parameters cannot be viewed on installed rivets. One parameter of interest is rivet concentricity. This parameter is measured by drilling out the rivet and making measurements of the uninstalled rivet. Drilling out the rivet destroys and removes the rivet. The drilling and measurements are a form of destructive testing.

As a result, destructive testing may be employed to obtain measurements for rivet concentricity and other parameters. With destructive testing, the disassembly and removal of rivets to make measurements is often more time consuming and more costly than desired. Another drawback with destructive testing, however, is that an additional step occurs in which another rivet is installed in the inspected location in the structure in the aircraft. This situation also increases the cost for manufacturing the commercial aircraft.

Therefore, it would be desirable to have a method and apparatus that take into account at least some of the issues discussed above, as well as other possible issues. For example, it would be desirable to have a method and apparatus that overcome a technical problem with obtaining measurements of desired parameters without using destructive testing.

SUMMARY

An illustrative embodiment of the present disclosure provides a method for automated non-destructive testing of rivet concentricity. A rivet is installed within a hole in a structure using an end effector. A first image of the hole in the structure and a second image of the rivet in the structure are processed to identify a number of reference points located in both the first image and the second image. The first image and the second image are aligned using the number of reference points. The first image is analyzed to determine a number of locations of the hole. The second image is analyzed to determine a number of locations of the rivet. A rivet concentricity is automatically determined using the number of locations of the hole and the number of locations of the rivet.

Another illustrative embodiment of the present disclosure provides an automated rivet measurement system. The automated rivet measurement system comprises a number of end effectors, a number of cameras, a processor, and a comparator. The number of end effectors is configured to perform drilling and riveting on a structure. The number of cameras is connected to the number of end effectors. The number of cameras is configured to take a first image of a hole in the structure and a second image of a rivet in the hole. The processor is configured to process the first image and the second image to identify a number of reference points in the first image and the second image. The comparator is configured to determine a rivet concentricity using the hole in the first image and the rivet in the second image, in which the first image and the second image are aligned using the number of reference points.

A further illustrative embodiment of the present disclosure provides a method for automated non-destructive testing of rivet concentricity. A hole is drilled in a structure using an end effector configured to perform drilling. A first image is taken of the hole in the structure. A rivet is installed within the hole using an end effector configured to perform riveting. A second image is taken of the rivet in the structure. The first image and the second image are processed to identify a number of reference points located in both the first image and the second image. The first image and the second image are aligned within a coordinate system relative to the number of reference points. The first image is analyzed to determine a number of locations of the hole. The second image is analyzed to determine a number of locations of the rivet. A rivet concentricity is automatically determined using the number of locations of the hole and the number of locations of the rivet.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

Figure 1:
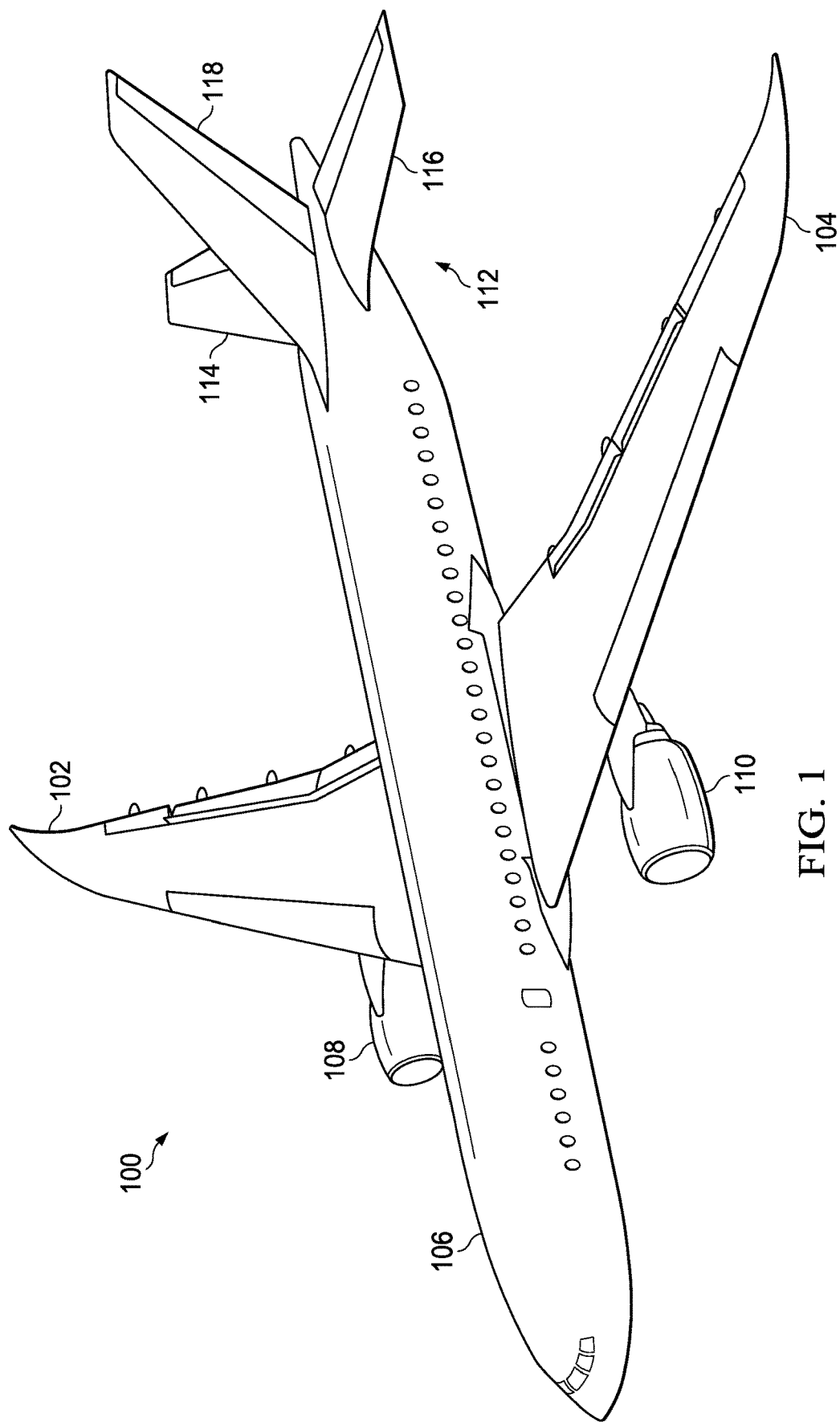
FIG. 1 is an illustration of an aircraft in which an illustrative embodiment may be implemented.

The illustrative embodiments recognize and take into account one or more different considerations. For example, the illustrative embodiments recognize and take into account that it would be desirable to perform measurements without destructive testing. The illustrative embodiments recognize and take into account one type of non-destructive testing that may be used to identify a rivet parameter, such as concentricity, is the use of an x-ray system.

The illustrative embodiments recognize and take into account, however, that an x-ray system is a less desirable non-destructive testing system. An x-ray system may require removal or disassembly of parts to perform x-ray measurements. After an image is generated, the parts are reinstalled or reassembled. In other cases, the removal or disassembly of parts may not be needed but the cost of the equipment, specialized training for operators, and time-consuming steps for x-ray measurements make this type of technique undesirable.

The illustrative embodiments recognize and take into account that reducing human exposure to x-rays is desirable. During operation of an x-ray system, human operators in range of the x-ray system within the manufacturing environment will be shielded from the x-rays. The illustrative embodiments recognize that x-ray inspections may be scheduled during times without scheduled manufacturing activities to minimize human operators in the manufacturing environment. The illustrative embodiments recognize that human operators within range of the x-ray system will be evacuated or shielded prior to operating the x-ray system. Evacuating or shielding human operators will result in work stoppage during operation of the x-ray system.

Thus, the illustrative embodiments recognize and take into account that an x-ray system is a less desirable non-destructive testing system because of the increase in time and effort needed to make measurements. The illustrative embodiments recognize that this type of system may increase the time and effort needed by great amounts when millions of rivets may be present.

The illustrative examples recognize and take into account that a rivet installed in a structure has a head and a button. The illustrative examples recognize and take into account that a head of a rivet is on an outer surface of the structure. The illustrative examples recognize and take into account that the outer surface of the structure is the surface through which the rivet is inserted for installation. The illustrative examples recognize and take into account that the inner surface of the structure is opposite to outer surface. The illustrative examples recognize and take into account that the inner surface is the surface on which the button forms when the rivet is installed.

The illustrative examples recognize and take into account that to install the rivet, the shaft of the rivet is inserted into a hole of the structure so that the head of the rivet contacts the outer surface of the structure. The illustrative examples recognize and take into account that the button is formed by contacting the shaft of the rivet and pressing downwards to deform the end of the rivet shaft into a button on the inner surface. The illustrative examples recognize and take into account that due to process variation, the button may be irregularly shaped. The illustrative examples recognize and take into account that due to process variation, the button may not be symmetric relative to the rivet shaft. The illustrative examples recognize and take into account that due to process variation, the button may not cover the hole.

The illustrative examples recognize and take into account that rivet concentricity describes how symmetrical the button is in the rivet. The illustrative examples recognize and take into account that rivet concentricity may be determined relative to the hole or relative to the rivet shaft.

The illustrative examples recognize and take into account that environmental factors influence the installation of rivets into a structure. The illustrative examples recognize and take into account that environmental factors may influence the concentricity of a resulting rivet.

The illustrative examples recognize and take into account that environmental factors may include a particular fastening machine, a particular team of human operators, or other suitable factors. The illustrative examples recognize and take into account that environmental factors also may include machine process parameters, for example, an installation process, hammering time, force exertion settings, drill speed, and other parameters. The illustrative examples recognize and take into account that these parameters may impact installations of rivets. The illustrative examples recognize and take into account that examples of environmental factors may include process parameters such as material type, coating, and drill bit wear. The illustrative examples recognize and take into account that additional environmental factors include temperature, humidity, machine location, and other types of environmental factors.

The illustrative embodiments recognize and take into account that performing non-destructive testing for rivet concentricity may take less time than performing measurements using destructive testing. The illustrative examples recognize and take into account that it may be desirable to perform inspections in situ. The illustrative embodiments recognize and take into account that performing non-destructive testing for rivet concentricity in situ may take less time than performing non-destructive testing as a separate step. The illustrative embodiments recognize and take into account that performing non-destructive testing for rivet concentricity in situ may include at least one of taking images, processing the images, or analyzing the images during other manufacturing operations. The illustrative embodiments recognize and take into account that performing non-destructive testing for rivet concentricity in situ may including performing non-destructive testing during at least one of drilling operations, riveting operations, or during movement between drilling or riveting operations.

The illustrative embodiments recognize and take into account that variability exists within manufacturing operations. The illustrative embodiments recognize and take into account that a tolerance exists for movement of end effectors within a manufacturing environment. The illustrative embodiments recognize and take into account that an end effector instructed to drive to the same location multiple times will not drive to precisely the same location each time due to movement tolerances. The illustrative embodiments recognize and take into account that images purportedly taken from the same location may have differences in position based on movement tolerances.

Referring now to the figures, and in particular, with reference to FIG. 1, an illustration of an aircraft is depicted in which an illustrative embodiment may be implemented. In this illustrative example, aircraft 100 has wing 102 and wing 104 connected to body 106. Aircraft 100 includes engine 108 connected to wing 102 and engine 110 connected to wing 104.

Body 106 has tail section 112. Horizontal stabilizer 114, horizontal stabilizer 116, and vertical stabilizer 118 are connected to tail section 112 of body 106.

Aircraft 100 is an environment in which rivets installed and measured by an automated rivet measurement system may be found. For example, rivets installed and measured by an automated rivet measurement system are present in at least one of wing 102, wing 104, or body 106.

As used herein, the phrase "at least one of", when used with a list of items, means different combinations of one or more of the listed items may be used, and only one of each item in the list may be needed. In other words, "at least one of" means any combination of items and number of items may be used from the list, but not all of the items in the list are required. The item may be a particular object, a thing, or a category.

For example, without limitation, "at least one of item A, item B, or item C" may include item A, item A and item B, or item C. This example also may include item A, item B, and item C; or item B and item C. Of course, any combinations of these items may be present. In some illustrative examples, "at least one of" may be, for example, without limitation, two of item A, one of item B, and ten of item C; four of item B and seven of item C; or other suitable combinations.

This illustration of aircraft 100 is provided for the purposes of illustrating one environment in which different illustrative embodiments may be implemented. The illustration of aircraft 100 in FIG. 1 is not meant to imply architectural limitations as to the manner in which different illustrative embodiments may be implemented. For example, aircraft 100 is shown as a commercial passenger aircraft. The different illustrative embodiments may be applied to other types of aircraft, such as a private passenger aircraft, rotorcraft, or other suitable types of aircraft.

Although the illustrative examples for an illustrative embodiment are described with respect to an aircraft, the illustrative embodiments may be applied to other types of structures. The structure may be, for example, a mobile structure, a stationary structure, a land-based structure, an aquatic-based structure, or a space-based structure. More specifically, the structure may be a surface ship, a tank, a personnel carrier, a train, a spacecraft, a space station, a satellite, a submarine, a manufacturing facility, a building, or other suitable types of structures.

Figure 2:
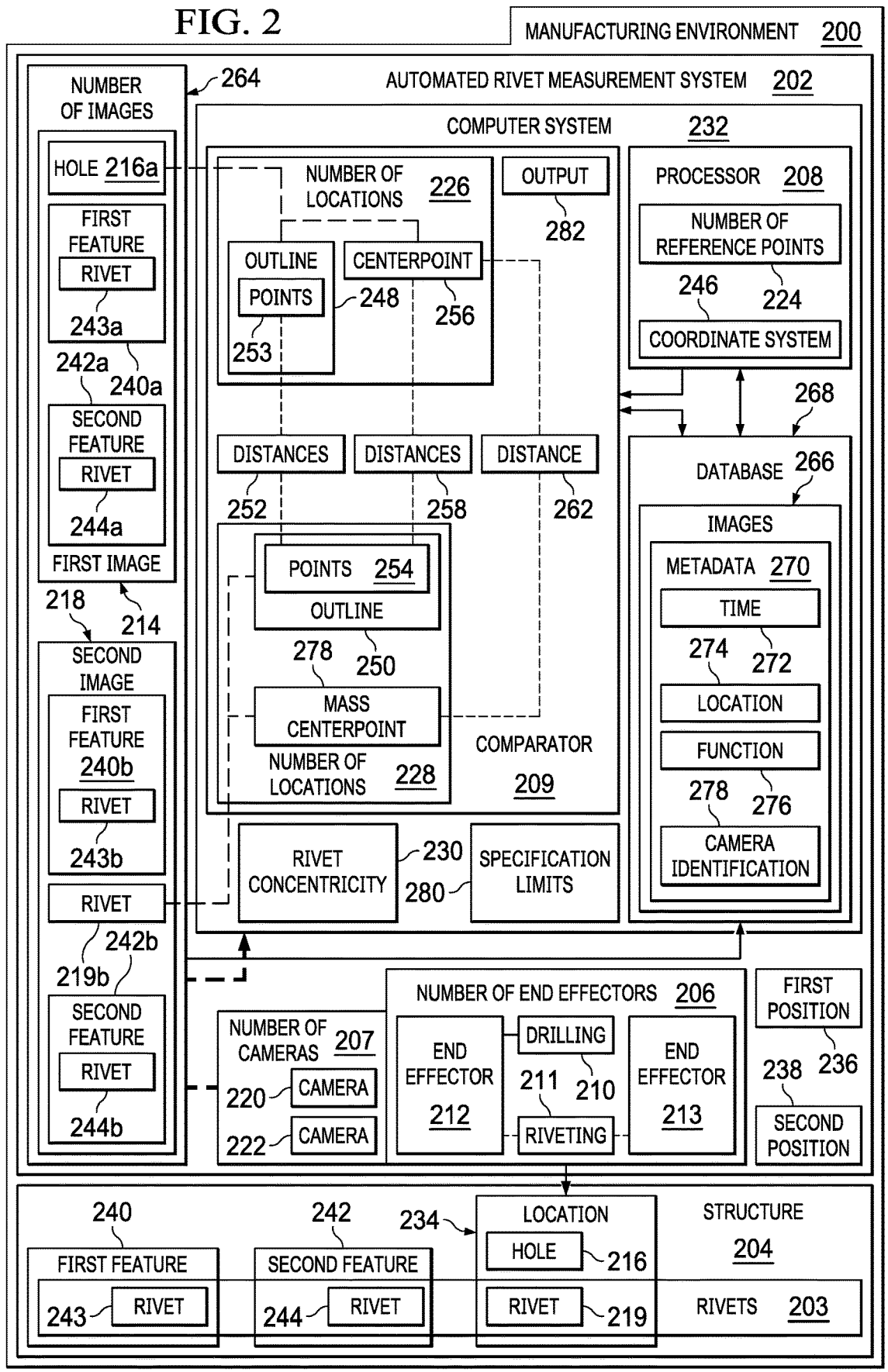
FIG. 2 is an illustration of a block diagram of a manufacturing environment with an automated rivet measurement system in accordance with an illustrative embodiment.

Turning now to FIG. 2, an illustration of a block diagram of a manufacturing environment with an automated rivet measurement system is depicted in accordance with an illustrative embodiment. Components of aircraft 100 may be manufactured in manufacturing environment 200. For example, at least one of wing 102 or wing 104 may have rivets installed and measured in manufacturing environment 200. In manufacturing environment 200, automated rivet measurement system 202 is used to install and measure rivets 203 in structure 204.

Structure 204 may take different forms. For example, a structure may be selected from at least one of a skin panel, a conduit, a monument, an engine, an engine housing, a fuselage section, a wing box, a spar, a rib, a line replaceable unit (LRU), an electrical assembly, and other types of structures that may be used in a vehicle. In this illustrative example, structure 204 may be formed from one or more parts or components that are connected to each other using rivets 203. In some illustrative examples, structure 204 may only be formed from a single part that includes rivets 203. In some illustrative examples, structure 204 is at least one part or component for use in aircraft 100.

Automated rivet measurement system 202 comprises number of end effectors 206, number of cameras 207, processor 208, and comparator 209. Number of end effectors 206 is configured to perform drilling 210 and riveting 211 on structure 204. As used herein, a "number of items" is one or more items. For example, number of end effectors 206 is one or more end effectors.

In some illustrative examples, number of end effectors 206 comprises one end effector to perform both drilling 210 and riveting 211. In these illustrative examples, number of end effectors 206 is end effector 212. In these illustrative examples, number of end effectors 206 is end effector 212 configured to perform both drilling 210 and riveting 211.

In other illustrative examples, number of end effectors 206 comprises more than one end effector to perform drilling 210 and riveting 211. In some illustrative examples, number of end effectors 206 is end effector 212 configured to perform drilling 210 and end effector 213 configured to perform riveting 211.

Number of cameras 207 is connected to number of end effectors 206. Number of cameras 207 is configured to take first image 214 of hole 216 in structure 204 and a second image 218 of rivet 219 in hole 216. First image 214 has hole 216a, a visual depiction of hole 216 in structure 204. Second image 218 has rivet 219b, a visual depiction of rivet 219 in structure 204.

In some illustrative examples, number of cameras 207 comprises camera 220 connected to end effector 212. In these illustrative examples, camera 220 takes both first image 214 and second image 218.

In some illustrative examples, number of cameras 207 comprises camera 220 connected to end effector 213. In these illustrative examples, camera 220 takes both first image 214 and second image 218.

In other illustrative examples, number of cameras 207 comprises camera 220 and camera 222. In these illustrative examples, camera 220 connected to end effector 212 takes first image 214. In these illustrative examples, camera 222 connected to end effector 213 takes second image 218.

In some illustrative examples, number of end effectors 206 comprises a first end effector, end effector 212, to perform drilling and a second end effector, end effector 213, to perform the riveting. In some of these illustrative examples, number of cameras 207 comprises camera 220 connected to the first end effector configured to take first image 214 and a second camera, camera 222, connected to the second end effector configured to take second image 218. In other of these illustrative examples, number of cameras 207 comprises camera 220 connected to the second end effector, end effector 213.

Processor 208 is configured to process first image 214 and second image 218 to identify number of reference points 224 in first image 214 and second image 218. Number of reference points 224 may take the form of any type of feature of structure 204. For example, number of reference points 224 may include at least one of a rivet, a hole, or an edge of structure 204.

Comparator 209 is configured to analyze first image 214 to determine number of locations 226 of hole 216a, analyze second image 218 to determine number of locations 228 of rivet 219b, and determine rivet concentricity 230 using number of locations 226 of hole 216a and number of locations 228 of rivet 219b. In some illustrative examples, number of locations 226 of hole 216a are a detected edge of hole 216a. In some illustrative examples, number of locations 226 may not be identical to an edge of hole 216. In some illustrative examples, number of locations 228 of rivet 219b are a detected edge of rivet 219b. In some illustrative examples, number of locations 228 may not be identical to an edge of the button of rivet 219.

Comparator 209 is a device configured to determine rivet concentricity 230. Comparator 209 is also configured to compare determined rivet concentricity 230 to specification limits 280.

As depicted, comparator 209 may be located in computer system 232. Computer system 232 is a physical hardware system and includes one or more data processing systems. When more than one data processing system is present, those data processing systems are in communication with each other using a communications medium. The communications medium may be a network. The data processing systems may be selected from at least one of a computer, a server computer, a tablet, or some other suitable data processing system.

In the illustrative examples, comparator 209 may be implemented in software, hardware, firmware, or a combination thereof. When software is used, the operations performed by comparator 209 may be implemented in program code configured to run on hardware, such as a processor unit. When firmware is used, the operations performed by comparator 209 may be implemented in program code and data, and stored in persistent memory to run on a processor unit. When hardware is employed, the hardware may include circuits that operate to perform the operations in comparator 209.

In the illustrative examples, the hardware may take a form selected from at least one of a circuit system, an integrated circuit, an application specific integrated circuit (ASIC), a programmable logic device, or some other suitable type of hardware configured to perform a number of operations. With a programmable logic device, the device may be configured to perform a number of operations. The device may be reconfigured at a later time or may be permanently configured to perform the number of operations. Programmable logic devices include, for example, a programmable logic array, a programmable array logic, a field programmable logic array, a field programmable gate array, and other suitable hardware devices. Additionally, the processes may be implemented in organic components integrated with inorganic components and may be comprised entirely of organic components. For example, the processes may be implemented as circuits in organic semiconductors.

End effector 212 drills hole 216 into location 234 of structure 204. In some illustrative examples, camera 220 is attached to end effector 212 and takes first image 214 when end effector 212 is at first position 236. In some illustrative examples, first position 236 is a position of end effector 212 to drill hole 216 into location 234. In some illustrative examples, first position 236 is a position of end effector 212 as end effector 212 moves away from location 234 after drilling 210 hole 216.

In some other illustrative examples, camera 220 is attached to end effector 213 and takes first image 214 when end effector 213 is at first position 236. In these illustrative examples, camera 220 takes first image 214 prior to end effector 213 performing riveting 211 to complete rivet 219.

One of end effector 212 or end effector 213 performs riveting 211 to complete rivet 219. Completing rivet 219 includes forming a button (not depicted) of rivet 219. The button (not depicted) of rivet 219 is the visible portion of rivet 219 that is imaged by number of cameras 207. Rivet concentricity 230 is determined using visual depictions of the button (not depicted) of rivet 219.

Number of cameras 207 takes second image 218 after rivet 219 is completed. In some illustrative examples, camera 220 attached to end effector 212 takes second image 218. In these illustrative examples, camera 220 takes second image 218 when end effector 212 is at second position 238.

In some illustrative examples, second position 238 is a position of end effector 212 to complete rivet 219 in hole 216. In some illustrative examples, second position 238 is a position of end effector 212 as end effector 212 moves away from rivet 219 after completing rivet 219 in hole 216.

In some illustrative examples, camera 220 is attached to end effector 213 and takes second image 218. In these illustrative examples, camera 220 takes second image 218 when end effector 213 is at second position 238.

In some illustrative examples, camera 222 is attached to end effector 213 and takes second image 218. In these illustrative examples, camera 222 takes second image 218 when end effector 213 is at second position 238.

In some illustrative examples, second position 238 is a position of end effector 213 to complete rivet 219 in hole 216. In some illustrative examples, second position 238 is a position of end effector 212 as end effector 213 moves away from rivet 219 after completing rivet 219 in hole 216.

In some illustrative examples, first position 236 and second position 238 are substantially the same. In some illustrative examples, first position 236 is offset from second position 238.

As depicted, structure 204 has first feature 240 and second feature 242. When first feature 240 and second feature 242 are present in two images, first feature 240 and second feature 242 may be used as number of reference points 224 for those two images. As depicted, first feature 240 and second feature 242 are present in two images, first image 214 and second image 218.

First feature 240a is a visual depiction of first feature 240 within first image 214. First feature 240b is a visual depiction of first feature 240 within second image 218.

Second feature 242a is a visual depiction of second feature 242 within first image 214. Second feature 242a is a visual depiction of second feature 242 within second image 218.

In this illustrative example, first feature 240 takes the form of rivet 243 of rivets 203. Rivet 243a is a visual depiction of rivet 243 within first image 214. Rivet 243b is a visual depiction of rivet 243 within second image 218.

In this illustrative example, second feature 242 takes the form of rivet 244 of rivets 203. Rivet 244a is a visual depiction of rivet 244 within first image 214. Rivet 244b is a visual depiction of rivet 244 within second image 218.

In other non-depicted examples, first feature 240 may be a hole (not depicted) in structure 204. In other non-depicted examples, first feature 240 may be an edge (not depicted) of structure 204. In other non-depicted examples, second feature 242 may be a hole (not depicted) in structure 204. In other non-depicted examples, second feature 242 may be an edge (not depicted) of structure 204.

Processor 208 aligns first image 214 and second image 218 using number of reference points 224. In some illustrative examples, processor 208 positions first image 214 relative to coordinate system 246. In some illustrative examples, processor 208 positions second image 218 relative to coordinate system 246.

In some illustrative examples, number of locations 226 of hole 216a are identified within coordinate system 246. In some illustrative examples, number of locations 228 of rivet 219b are identified within coordinate system 246.

In some illustrative examples, first image 214 and second image 218 are aligned using number of reference points 224 prior to overlaying second image 218 and first image 214. In some illustrative examples, first image 214 and second image 218 are aligned using number of reference points 224 prior to overlaying number of locations 226 of hole 216a onto second image 218.

Comparator 209 automatically determines rivet concentricity 230 at any desirable time. In some illustrative examples, comparator 209 determines rivet concentricity 230 in situ. When comparator 209 determines rivet concentricity 230 in situ, comparator 209 determines rivet concentricity 230 while number of end effectors 206 is performing operations on structure 204. In some illustrative examples, when comparator 209 determines rivet concentricity 230 in situ, comparator 209 determines rivet concentricity 230 while number of end effectors 206 is performing drilling 210 and riveting 211 on structure 204. In some illustrative examples, comparator 209 determines rivet concentricity 230 in response to receiving first image 214 and second image 218. In some illustrative examples, comparator 209 determines rivet concentricity 230 in response to number of end effectors 206 completing drilling 210 and riveting 211 on structure 204. In some illustrative examples, comparator 209 determines rivet concentricity 230 of rivet 219 in response to number of end effectors 206 completing drilling 210 and riveting 211 on location 234 of structure 204.

Comparator 209 performs any desirable procedures to determine rivet concentricity 230. In some illustrative examples, comparator 209 is configured to create outline 248 of hole 216a and create outline 250 of rivet 219b. Outline 248 is representative of number of locations 226 of hole 216a. Outline 250 is representative of number of locations 228 of rivet 219b. In some illustrative examples, determining rivet concentricity 230 comprises determining distances 252 between points 253 of outline 248 of hole 216a and points 254 of outline 250 of rivet 219b. In some illustrative examples, rivet concentricity 230 is a smallest value of distances 252.

In some illustrative examples, distances 252 include distances between each of points 253 and each of points 254. In other illustrative examples, distances 252 include distances between each of points 254 and a subset of points 253 for each point of points 254. In other illustrative examples, distances 252 include distances perpendicular to tangents of outline 248.

In some illustrative examples, comparator 209 is configured to create outline 248 of hole 216a, determine centerpoint 256 of outline 248 of hole 216a, and create outline 250 of rivet 219b. In some illustrative examples, determining rivet concentricity 230 comprises determining distances 258 between points 254 of outline 250 of rivet 219a and centerpoint 256. In some illustrative examples, rivet concentricity 230 is a smallest value of distances 258.

In some illustrative examples, comparator 209 is configured to create outline 248 of hole 216a, determine centerpoint 256 of outline 248 of hole 216a, create outline 250 of rivet 219b, and determine mass centerpoint 260 of outline 250 of rivet 219b. In some illustrative examples, determining rivet concentricity 230 comprises determining distance 262 between centerpoint 256 and mass centerpoint 260.

Number of cameras 207 takes number of images 264 as number of end effectors 206 perform drilling 210 and riveting 211 on structure 204. Number of images 264 are sent to computer system 232 for processing by processor 208 and analysis by comparator 209. Number of images 264 may include any desirable quantity of images. Number of images 264 may be stored as images 266 within database 268.

Automated rivet measurement system 202 may use metadata 270 of images 266 to determine which of images 266 to process to identify number of reference points 224. For example, each of images 266 may have two completed rivets of rivets 203 in similar locations that may be used as number of reference points 224. However, each rivet of rivets 203 will have a uniquely shaped and positioned button (not depicted). To reduce processing resources, subsets of images 266 may be eliminated as unrelated.

The two images of images 266 including a hole and a rivet later installed with the hole may be identified using metadata 270. For example, first image 214 and second image 218 to be processed and analyzed may be identified using metadata 270.

In some illustrative examples, first image 214 is identified as having hole 216a using at least one of time 272 first image 214 was taken, location 274 within manufacturing environment 200, function 276, or camera identification 278. In some illustrative examples, location 274 is a location of the camera of number of cameras 207 that took first image 214. In some illustrative examples, location 274 is a location of the end effector of number of end effectors 206 the respective camera of number of cameras 207 that took first image 214 is attached to. Location 274 may be identified using any desirable method. In some illustrative examples, location 274 is identified using positional sensors within manufacturing environment 200.

Function 276 is a manufacturing function, such as drilling 210 or riveting 211, that is performed either prior to or during taking of first image 214. Camera identification 278 is a unique identifier for the camera of number of cameras 207 that took first image 214.

Processor 208 identifies first image 214 using metadata 270. Processor 208 identifies second image 218 using metadata 270. For example, time 272 of second image 218 will be later than time 272 of first image 214. In some illustrative examples, location 274 of first image 214 will be substantially the same as location 274 of second image 218. In some illustrative examples, location 274 of first image 214 and location 274 of second image 218 are such that first feature 240, second feature 242, and location 234 are visible in first image 214 and second image 218.

Comparator 209 automatically determines if rivet concentricity 230 satisfies specification limits 280. In some illustrative examples, comparator 209 generates output 282 indicating whether rivet 219 satisfies specification limits 280.

In some illustrative examples, output 282 is an alert or an alarm. Output 282 may trigger an audio or visual alarm when rivet concentricity 230 does not satisfy specification limits 280. In some illustrative examples, output 282 is an entry in a report. In some illustrative examples, output 282 is part of a map of locations of structure 204 that do not satisfy specification limits 280.

In some illustrative examples, when output 282 indicates that rivet concentricity 230 of rivet 219 does not satisfy specification limits 280, output 282 will be reviewed by an operator. In some illustrative examples, when output 282 indicates that rivet concentricity 230 of rivet 219 does not satisfy specification limits 280, rivet 219 will be reworked.

In one illustrative example, one or more technical solutions are present that overcome a technical problem with obtaining measurements of desired parameters without using destructive testing. As a result, one or more technical solutions may provide a technical effect to identifying destructive testing measurements without having to perform destructive testing. One or more technical solutions are present that provide an ability to identify a rivet concentricity without drilling out the rivet.

As a result, computer system 232 operates as a special purpose computer system in which comparator 209 in computer system 232 enables determining a rivet concentricity from images in situ. In particular, comparator 209 transforms computer system 232 into a special purpose computer system, as compared to currently available general computer systems that do not have comparator 209.

The illustration of manufacturing environment 200 in FIG. 2 is not meant to imply physical or architectural limitations to the manner in which an illustrative embodiment may be implemented. Other components, in addition to or in place of the ones illustrated, may be used. Some components may be unnecessary. Also, the blocks are presented to illustrate some functional components. One or more of these blocks may be combined, divided, or combined and divided into different blocks when implemented in an illustrative embodiment.

In some illustrative examples, structure 204 may include other non-depicted features. For example, rivets 203 in structure 204 may include more than three rivets. In some illustrative examples, number of reference points 224 includes more than two reference points. For example, number of reference points 224 may include three reference points.

Figure 3:
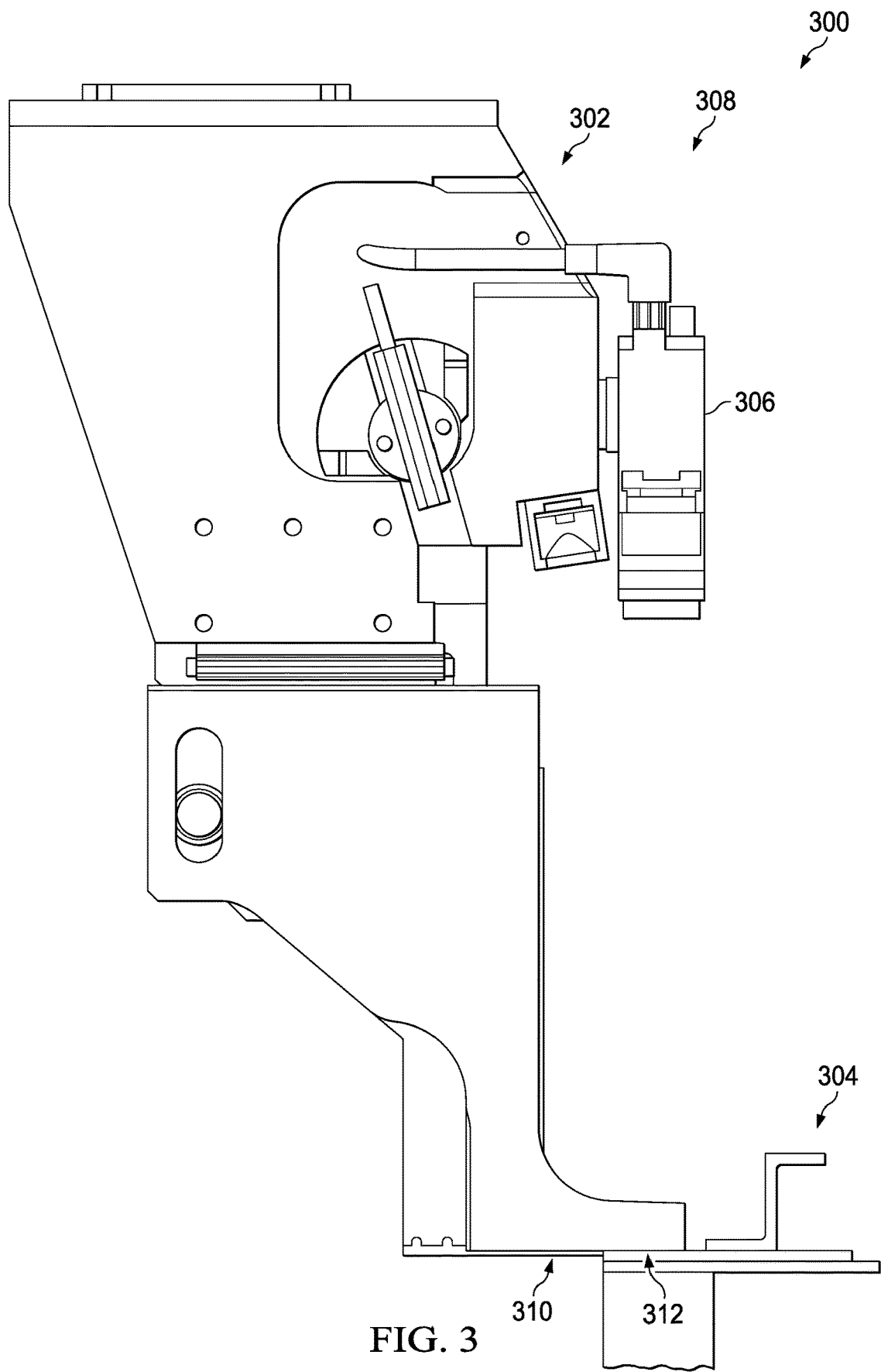
FIG. 3 is an illustration of an isometric view of a manufacturing environment with an automated rivet measurement system in accordance with an illustrative embodiment.

Turning now to FIG. 3, an illustration of a side view of a manufacturing environment with an automated rivet measurement system is depicted in accordance with an illustrative embodiment. Manufacturing environment 300 is one physical implementation of manufacturing environment 200 of FIG. 2. End effector 302 in manufacturing environment 300 is a physical implementation of end effector 213 of FIG. 2.

In this illustrative example, end effector 302 is configured to performing riveting operations. In this illustrative example, end effector 302 is positioned to install rivets in holes (not depicted) in structure 304 in manufacturing environment 300. In this illustrative example, a different end effector (not depicted) is used to drill holes in structure 304.

End effector 302 and camera 306 are components of automated rivet measurement system 308. In this illustrative example, camera 306 is a physical implementation of a camera of number of cameras 207 of FIG. 2. In some illustrative examples, camera 306 is an implementation of camera 220 that takes images of holes and rivets, such as first image 214 and second image 218. In some illustrative examples, camera 306 is an implementation of camera 222 that takes image of installed rivets, such as second image 218. Automated rivet measurement system 308 automatically determines rivet concentricity in situ using at least one image from camera 306.

Camera 306 takes images of structure 304 during operation of end effector 302. In one illustrative example, camera 306 takes images before and after a riveting operation at a hole. In this illustrative example, camera 306 takes both a first image, such as first image 700 of FIG. 7, and a second image, such as second image 800 of FIG. 8. In this illustrative example, camera 306 takes the first image when end effector 302 is at a first position and the second image when end effector 302 is at a second position. In some illustrative examples, the first position and the second position are substantially the same. In other illustrative examples, the first position and the second position are offset from each other.

In another illustrative example, camera 306 takes an image after installing a rivet in a hole. In this illustrative example, camera 306 may take only a second image, such as second image 800 of FIG. 8. In this illustrative example, camera 306 takes the second image when end effector 302 is at a second position. In this illustrative example, a different camera attached to another end effector (not depicted) configured to drill holes in structure 304 takes a first image when the other end effector is at a first position. In some illustrative examples, the first position and the second position are substantially the same. In other illustrative examples, the first position and the second position are offset from each other.

When first position and second position are substantially the same, first image and second image may still be aligned due to end effector movement tolerances. When first position and second position are offset, first image and second image are registered or aligned due to the offset between the first position and the second position.

The illustration of automated rivet measurement system 308 in FIG. 3 is not meant to imply architectural limitations as to the manner in which different illustrative embodiments may be implemented. For example, in other non-depicted examples, an end effector (not depicted) both drills a hole into structure 304 and installs a rivet in the hole. In these non-depicted examples, a camera attached to the end effector (not depicted) takes images of both the hole and the rivet. In these illustrative examples, the camera takes a first image when the end effector is in a first position relative to structure 304. After drilling the hole in structure 304, the camera will take a second image when the end effector is at a second position. In some illustrative examples, the first position and the second position are substantially the same. In some illustrative examples, the first position is a drilling position and the second position is a riveting position. In some illustrative examples, the first position is a position of the end effector after drilling. In some illustrative examples, the second position is a position of the end effector after riveting.

Figure 4:
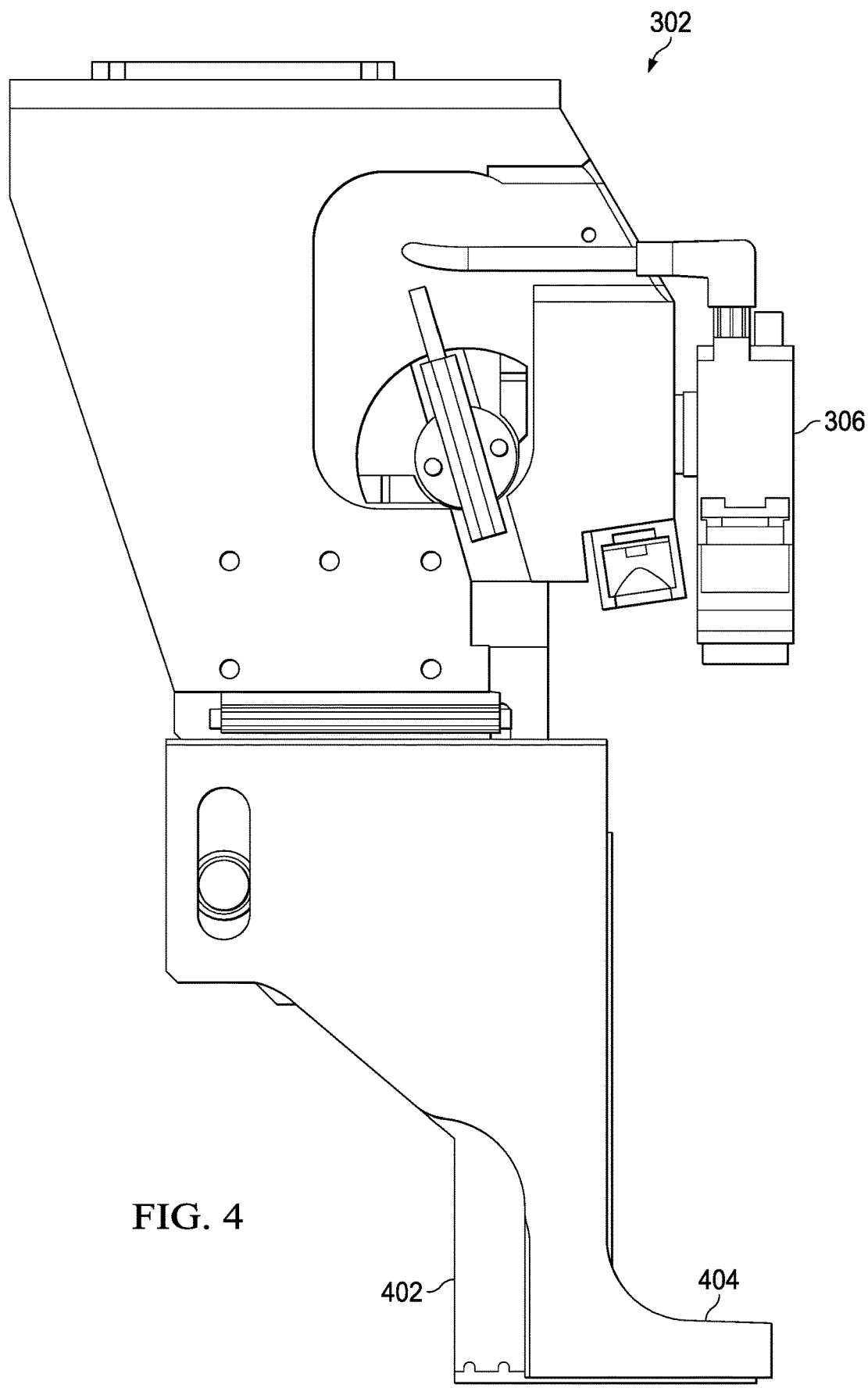
FIG. 4 is an illustration of an end effector with a connected camera in accordance with an illustrative embodiment.

Turning now to FIG. 4, an illustration of an end effector with a connected camera is depicted in accordance with an illustrative embodiment. View 400 is a view of a side view of end effector 302 of FIG. 3.

Camera 306 is connected to end effector 302 and moves with end effector 302. As end effector 302 moves relative to a structure, such as structure 304 of FIG. 3, camera 306 is also moved relative to the structure.

End effector 302 has clamp foot 402 and bucking tool 404. During riveting, bucking tool 404 contacts a rivet to form a button.

Figure 5:
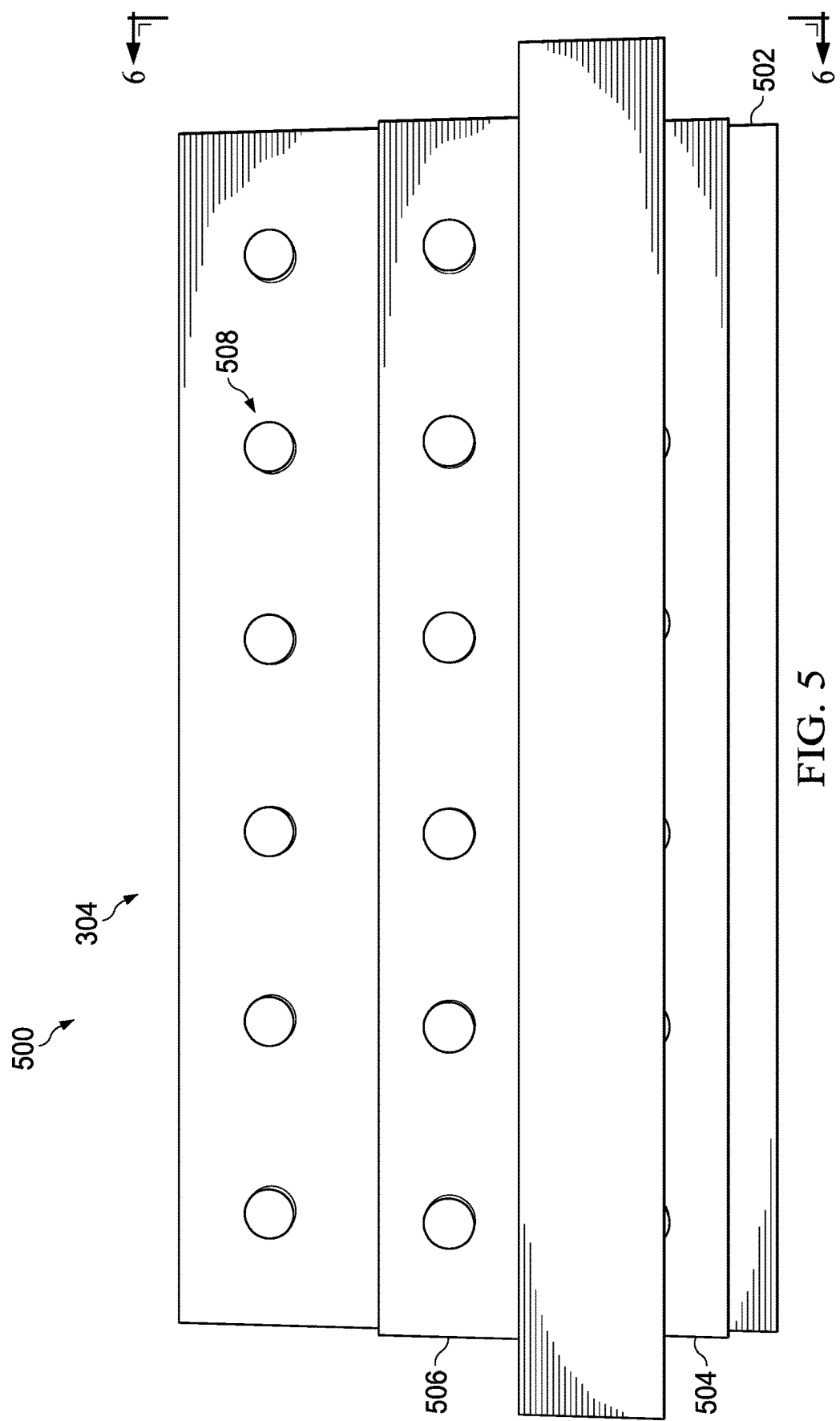
FIG. 5 is an illustration of a top view of a structure with installed rivets in accordance with an illustrative embodiment.

Turning now to FIG. 5, an illustration of a top view of a structure with installed rivets is depicted in accordance with an illustrative embodiment. View 500 is a top view of structure 304 of FIG. 3. Structure 304 is a physical implementation of structure 204 of FIG. 2.

In this illustrative example, structure 304 is formed of three components riveted together. As depicted, structure 304 is formed of first plate 502, second plate 504, and beam 506. Each of first plate 502, second plate 504, and beam 506 are head together using rivets 508. Rivets 508 are installed and measured using automated rivet measurement system 308 of FIG. 3.

Figure 6:
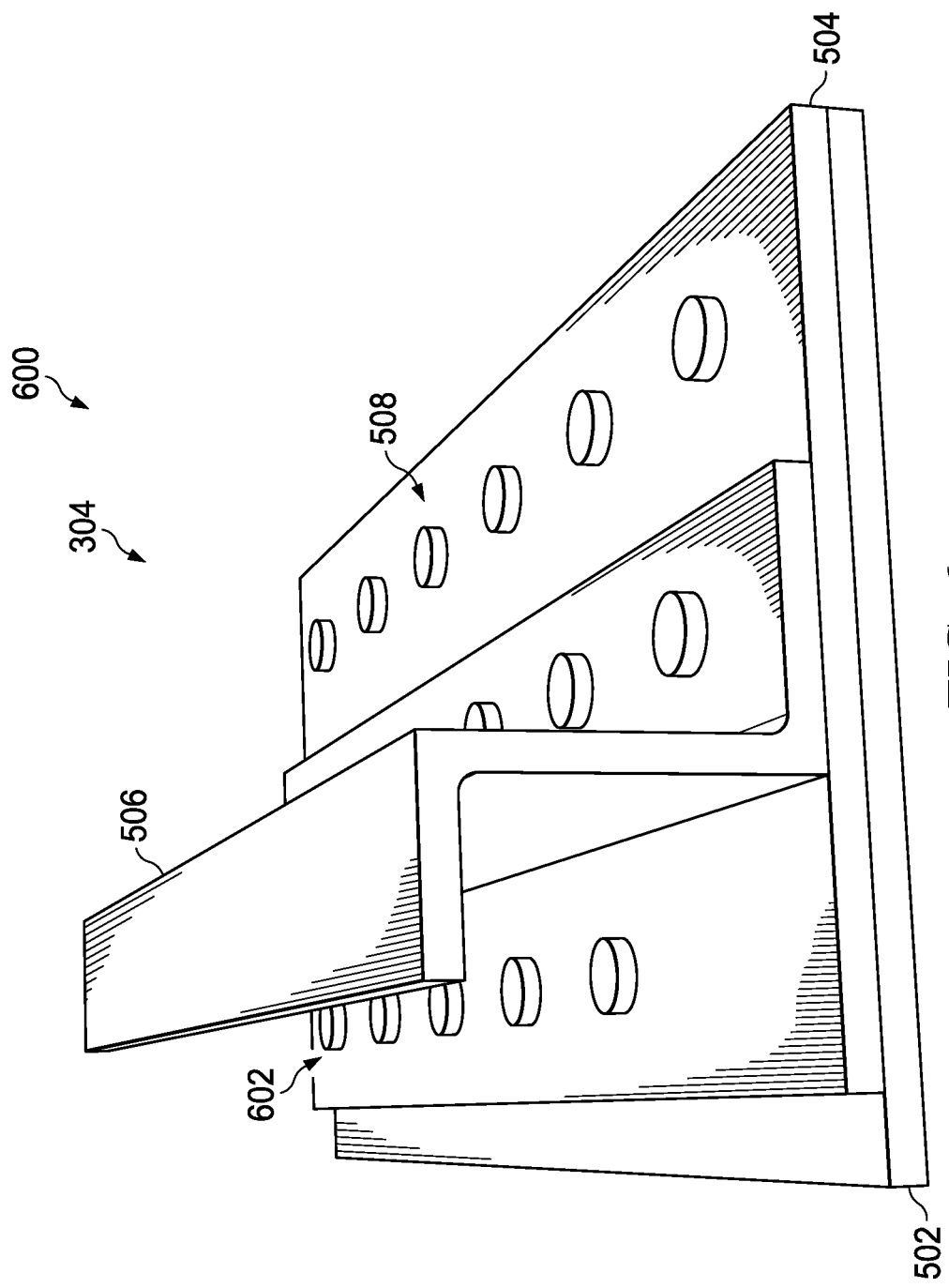
FIG. 6 is an illustration of a perspective view of a structure with installed rivets in accordance with an illustrative embodiment.

Turning now to FIG. 6, an illustration of a perspective view of a structure with installed rivets is depicted in accordance with an illustrative embodiment. View 600 is a perspective view of structure 304 of FIG. 3.

In view 600, rivets 602 shielded by beam 506 in view 500 are seen. To measure rivets 602, images are taken by camera 306 of FIG. 3 at an angle relative to structure 304. Automated rivet measurement system 308 provides compensation for the angle during image processing and image analysis. Rivets 604 of rivets 508 may be measured using images of a top view of structure 304.

Figure 7:
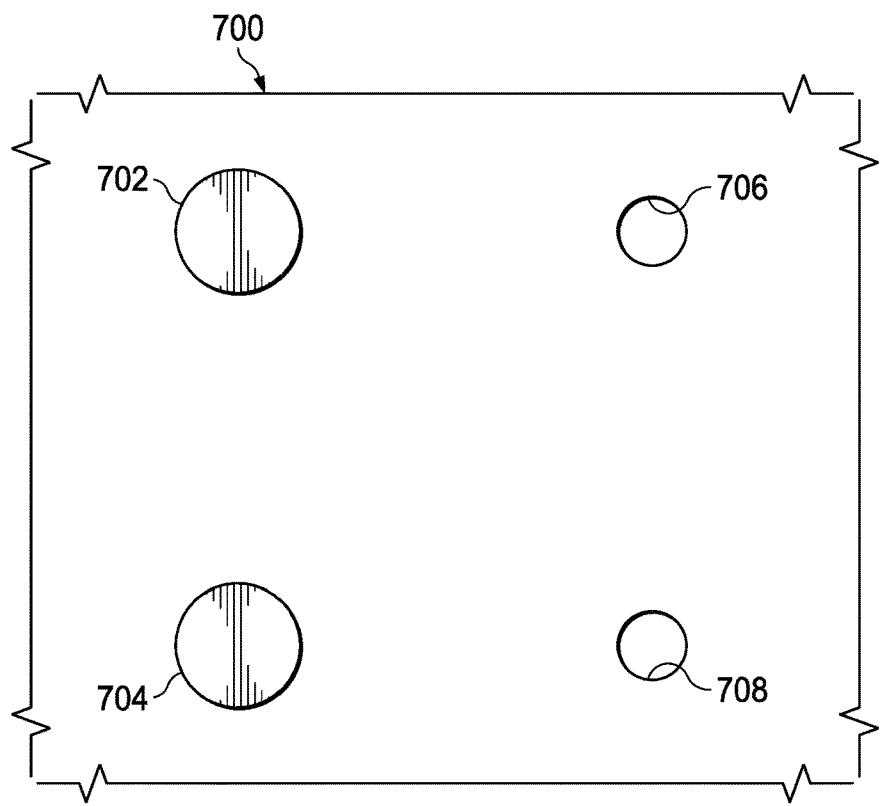
FIG. 7 is an illustration of a first image in accordance with an illustrative embodiment.

Turning now to FIG. 7, an illustration of a first image is depicted in accordance with an illustrative embodiment. First image 700 is an implementation of first image 214 of FIG. 2. First image 700 is an image of a structure, such as structure 304 of FIGS. 3, 5, and 6.

First image 700 has rivet 702, rivet 704, hole 706, and hole 708. Any of rivet 702, rivet 704, hole 706, or hole 708 may be a reference point for first image 700.

Rivet 702 is a visual depiction within first image 700 of a physical rivet. Rivet 704 is a visual depiction within first image 700 of a physical rivet. Hole 706 is a visual depiction within first image 700 of a physical hole. Hole 708 is a visual depiction within first image 700 of a physical hole.

When first image 700 is taken, metadata is saved along with first image 700. The metadata includes data to uniquely identify first image 700. The metadata includes at least one of camera identification, a location of the camera in a coordinate system, a time, a date, a function performed by the end effector prior to taking first image 700, or any other desirable data.

Figure 8:
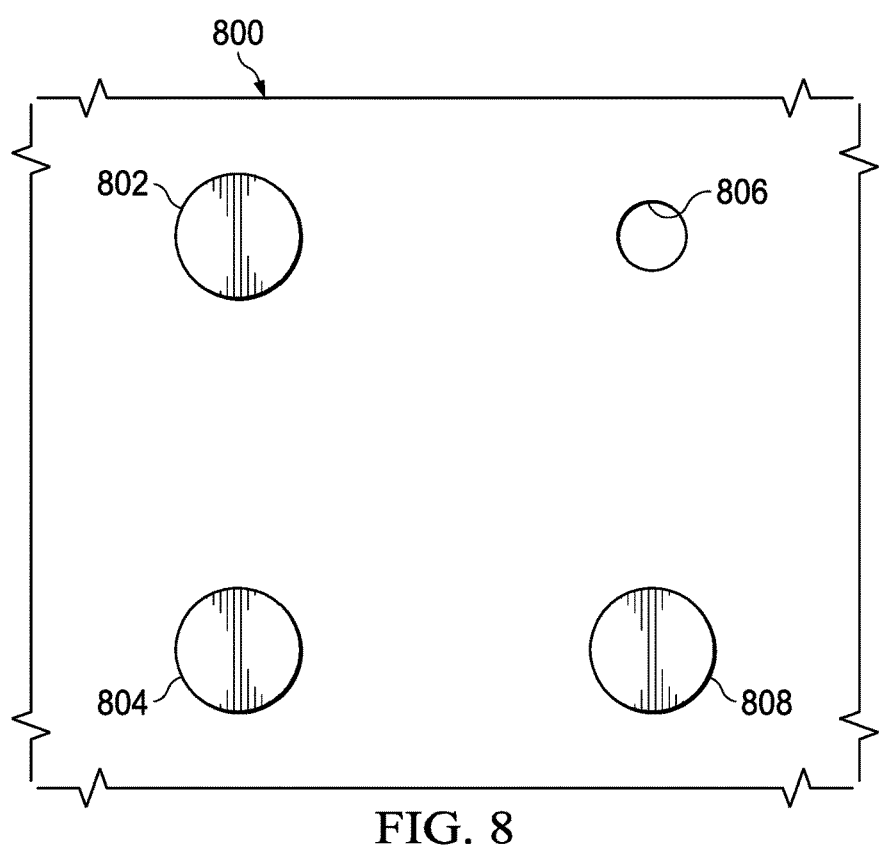
FIG. 8 is an illustration of a second image in accordance with an illustrative embodiment.

Turning now to FIG. 8, an illustration of a second image is depicted in accordance with an illustrative embodiment. Second image 800 is an image of a structure, such as structure 304 of FIGS. 3, 5, and 6. Second image 800 is an implementation of second image 218 of FIG. 2. In some illustrative examples, second image 800 is an image of the same structure as in FIG. 7. In some illustrative examples, second image 800 is an image of the same location as imaged in FIG. 7. Second image 800 has rivet 802, rivet 804, hole 806, and rivet 808.

Rivet 802 is a visual depiction within second image 800 of a physical rivet. Rivet 804 is a visual depiction within second image 800 of a physical rivet. Hole 806 is a visual depiction within second image 800 of a physical hole. Rivet 808 is a visual depiction within second image 800 of a physical rivet.

When second image 800 is taken, metadata is saved along with second image 800. The metadata includes data to uniquely identify second image 800. The metadata includes at least one of camera identification, a location of the camera in a coordinate system, a time, a date, a function performed by the end effector prior to taking second image 800, or any other desirable data.

Metadata for second image 800 is compared to metadata for other images to determine any potentially related images. When compared to metadata for first image 700, metadata for second image 800 may indicate that first image 700 and second image 800 include at least some of the same features.

Figure 9:
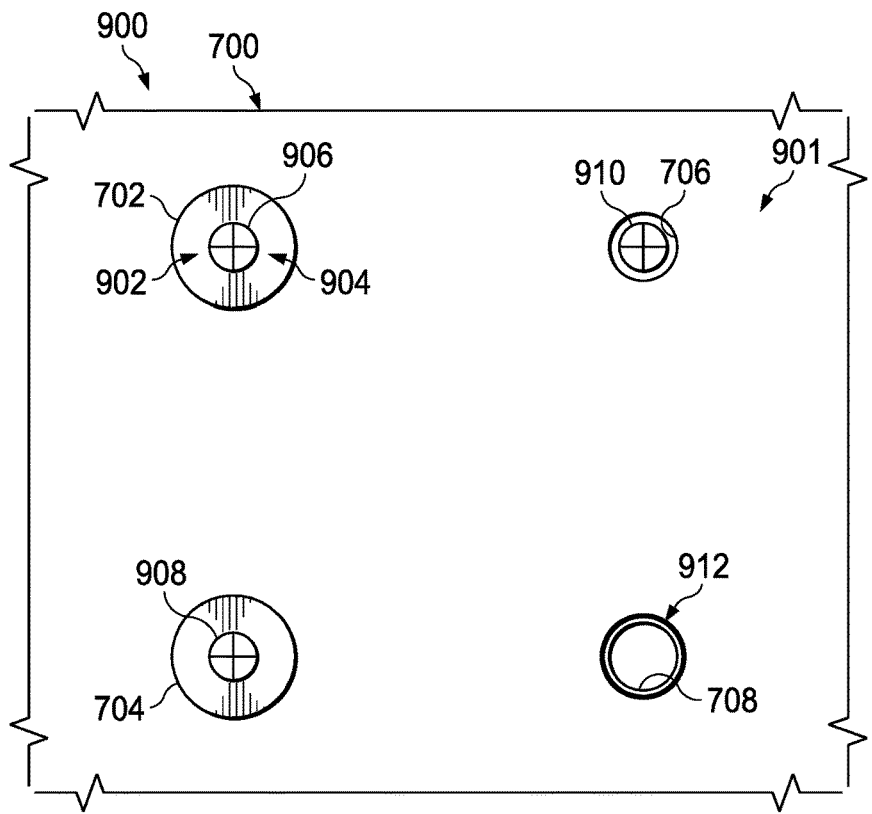
FIG. 9 is an illustration of a first image after processing in accordance with an illustrative embodiment.
Figure 10:
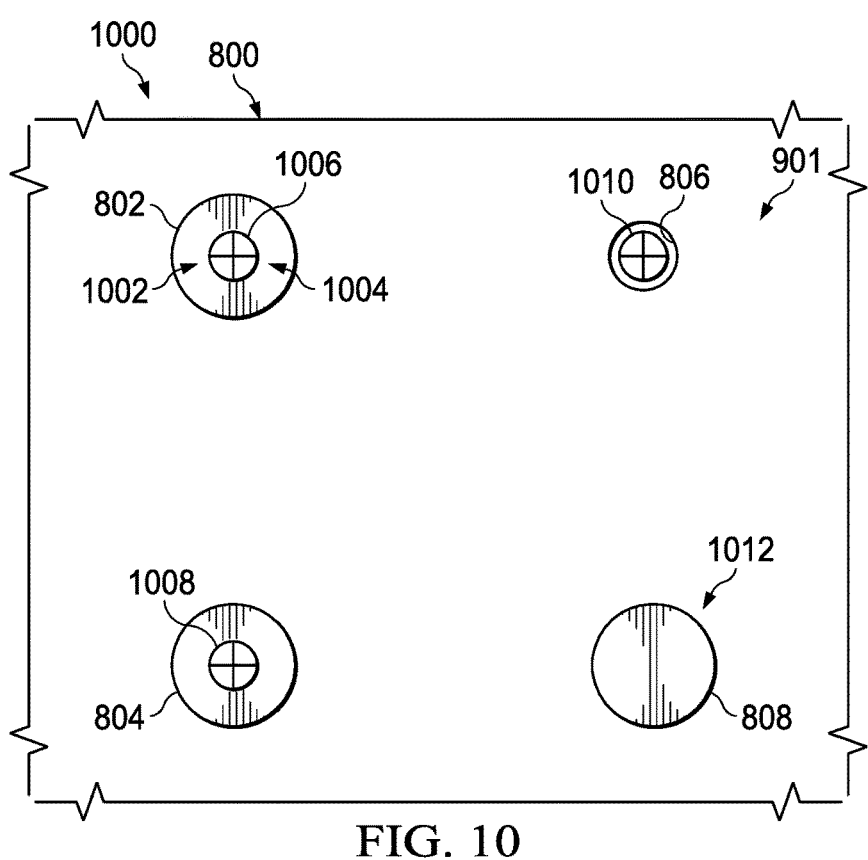
FIG. 10 is an illustration of a second image after processing in accordance with an illustrative embodiment.
Figure 11:
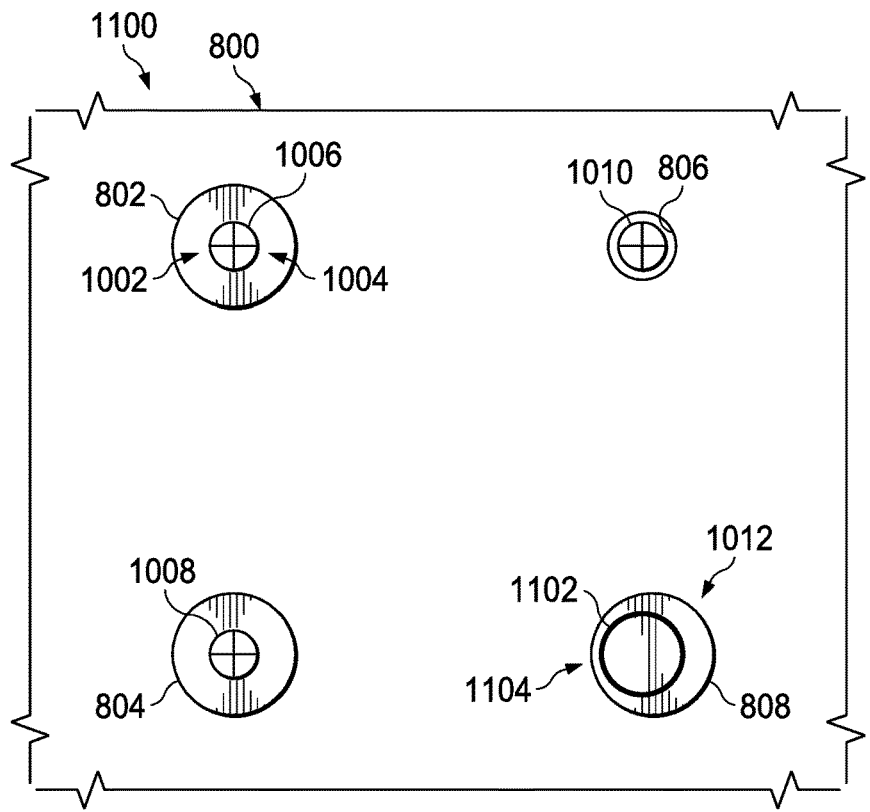
FIG. 11 is an illustration of a second image after processing in accordance with an illustrative embodiment.

For illustrative purposes, first image 700 and second image 800 are visual depictions of the same location of a structure before and after installing a rivet. FIGS. 9-11 depict image analysis using illustrative markings over first image 700 and second image 800. Although first image 700 and second image 800 are depicted and discussed as images of approximately the same location of a structure, in some illustrative examples, first image 700 and second image 800 may be images of different locations of the same or different structures.

Turning now to FIG. 9, an illustration of a first image after processing is depicted in accordance with an illustrative embodiment. View 900 is a view of first image 700 with illustrative markings overlaid.

First image 700 and second image 800 are views of the same location of structure 901 at two different times. First image 700 is taken after drilling hole 708. Second image 800 is taken after inserting rivet 808 into hole 708.

In some illustrative examples, only metadata may be used to identify first image 700 and second image 800 as containing the same features. In other illustrative examples, metadata may be used in conjunction with visual data of first image 700 and second image 800 to identify first image 700 and second image 800 as containing the same features. For example, after identifying first image 700 and second image 800 as possibly containing the same features, visual data of first image 700 and second image 800 may be compared to identify inconsistencies or other unique characteristics present in both first image 700 and second image 800.

For example, visual data of first image 700 and second image 800 may be used to confirm that rivet 702 is the same as rivet 802. For example, a divot is present in each of rivet 702 and rivet 802.

First image 700 is processed to determine number of reference points 902. Number of reference points 902 include features present in both first image 700 and second image 800. Rivet 702 is the same as rivet 802 in second image 800. Rivet 704 is the same as rivet 804 in second image 800. Hole 706 is the same as hole 806 in second image 800. Hole 708 is not seen in second image 800.

Number of reference points 902 include rivet 702, rivet 704, and hole 706. In view 900 illustrative markings 904 are representative of number of reference points 902. Illustrative markings 904 representative of number of reference points 902 are overlaid on rivet 702, rivet 704, hole 706.

For example, illustrative marking 906 is overlaid on rivet 702. Illustrative marking 908 is overlaid on rivet 704. Illustrative marking 910 is overlaid on hole 706.

Number of reference points 902 are used to register first image 700. In some illustrative examples, number of reference points 902 are used to position first image 700 relative to a coordinate system.

After processing first image 700, first image 700 is analyzed. First image 700 is analyzed to determine number of locations 912 of hole 708.

Number of reference points 902 may include any desirable type of features present in first image 700. Although not depicted in first image 700, number of reference points 902 could include an edge of structure 901, an inconsistency of structure 901, a marking, or any other desirable feature.

Turning now to FIG. 10, an illustration of a second image after processing is depicted in accordance with an illustrative embodiment. View 1000 is a view of second image 800 with illustrative markings overlaid.

First image 700 and second image 800 are views of the same location of structure 901 at two different times. First image 700 is taken after drilling hole 708. Second image 800 is taken after inserting rivet 808 into hole 708.

Second image 800 is processed to determine number of reference points 1002. Number of reference points 1002 include features present in both first image 700 and second image 800. Rivet 802 is the same as rivet 702 in first image 700. Rivet 804 is the same as rivet 704 in first image 700. Hole 806 is the same as hole 706 in first image 700. Rivet 808 is not seen in first image 700.

Number of reference points 1002 include rivet 802, rivet 804, and hole 806. In view 1000 illustrative markings 1004 are representative of number of reference points 1002. Illustrative markings 1004 representative of number of reference points 1002 are overlaid on rivet 802, rivet 804, hole 806.

For example, illustrative marking 1006 is overlaid on rivet 802. Illustrative marking 1008 is overlaid on rivet 804. Illustrative marking 1010 is overlaid on hole 806.

Number of reference points 1002 are used to register second image 800. In some illustrative examples, number of reference points 1002 are used to position second image 800 relative to a same coordinate system as first image 700.

After processing second image 800, second image 800 is analyzed. Second image 800 is analyzed to determine number of locations 1012 of rivet 808.

Turning now to FIG. 11, an illustration of a second image after processing is depicted in accordance with an illustrative embodiment. View 1100 is a view of second image 800 with number of reference points 1002 and outline 1102. Outline 1102 comprises points 1104 representative of hole 708 of first image 700. Outline 1102 is representative of number of locations 912 in FIG. 9 of hole 708.

Figure 12:
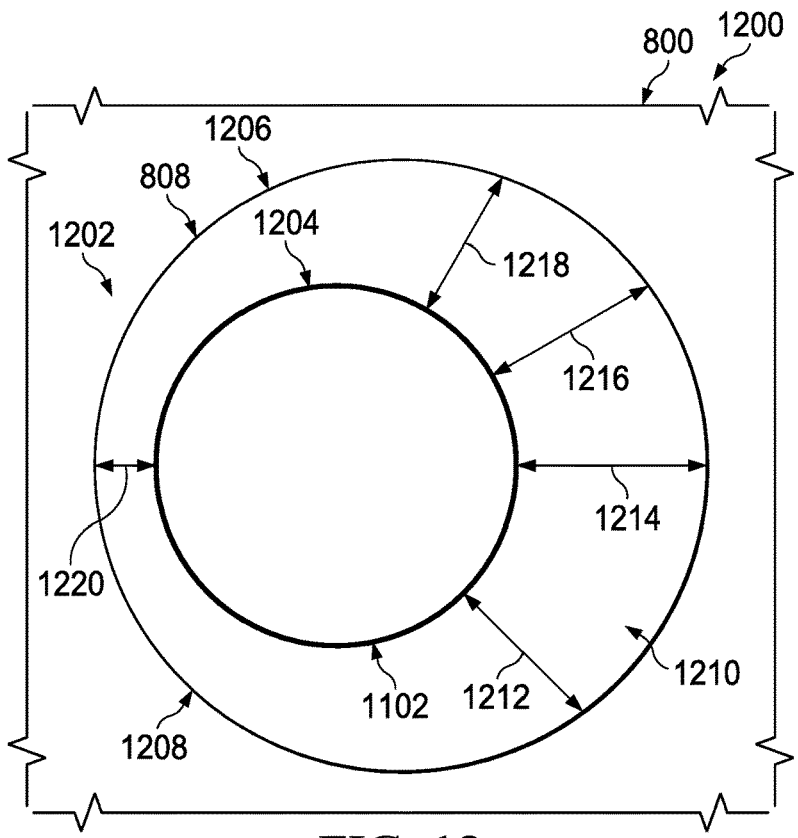
FIG. 12 is an illustration of representative analysis overlaid on a portion of a second image in accordance with an illustrative embodiment.

Turning now to FIG. 12, an illustration of representative analysis overlaid on a portion of a second image is depicted in accordance with an illustrative embodiment. View 1200 is a view of rivet 808 of second image 800 with representative analysis 1202.

Representative analysis 1202 is a series of visual indicators of analysis performed by comparator 209 of FIG. 2.

As discussed above with reference to FIG. 9, an analysis is performed to determine number of locations 912 of hole 708 of FIG. 9. Number of locations 912 of hole 708 are a detected edge of hole 708.

As discussed above with reference to FIG. 10, an analysis is performed to determine number of locations 1012 of rivet 808. Number of locations 1012 of rivet 808 are a detected edge of the button of rivet 808.

Representative analysis 1202 includes outline 1102. Outline 1102 comprises points 1204 representative of hole 708 of first image 700. As depicted, outline 1102 is approximately circular. Points 1204 correspond approximately to number of locations 912 of hole 708 of FIG. 7.

Outline 1206 comprises points 1208 representative of rivet 808 of second image 800. As depicted, outline 1206 and rivet 808 are irregular. Points 1208 correspond approximately to number of locations 1012 of rivet 808 of FIG. 10.

In this illustrative example, determining the rivet concentricity comprises determining distances 1210 between points 1204 of outline 1102 of hole 708 and points 1208 of outline 1206 of rivet 808. In this illustrative example, the rivet concentricity is a smallest value of distances 1210.

Representative analysis 1202 includes distance 1212, distance 1214, distance 1216, distance 1218, and distance 1220. Although only five distances are depicted, any desirable number of distances may be determined. In this illustrative example, distance 1220 is the smallest value. In this illustrative example, distance 1220 is set as the rivet concentricity.

Figure 13:
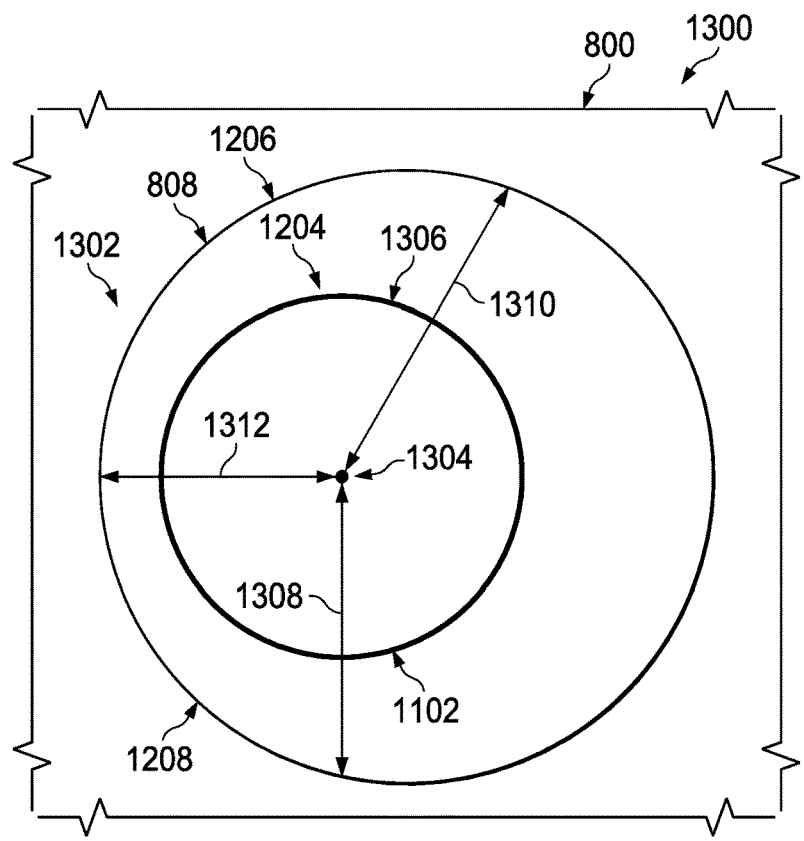
FIG. 13 is an illustration of representative analysis overlaid on a portion of a second image in accordance with an illustrative embodiment.

Turning now to FIG. 13, an illustration of representative analysis overlaid on a portion of a second image is depicted in accordance with an illustrative embodiment. View 1300 is a view of rivet 808 of second image 800 with representative analysis 1302. Representative analysis 1302 is a series of visual indicators of analysis performed by comparator 209 of FIG. 2.

As discussed above with reference to FIG. 9, an analysis is performed to determine number of locations 912 of hole 708. Number of locations 912 of hole 708 are a detected edge of hole 708.

As discussed above with reference to FIG. 10, an analysis is performed to determine number of locations 1012 of rivet 808. Number of locations 1012 of rivet 808 are a detected edge of the button of rivet 808.

Representative analysis 1302 includes outline 1102. Outline 1102 comprises points 1204 representative of hole 708 of first image 700. As depicted, outline 1102 is approximately circular. Points 1204 correspond approximately to number of locations 912 of hole 708 of FIG. 7. Centerpoint 1304 of outline 1102 of hole 708 is determined during the analysis.

Outline 1206 comprises points 1208 representative of rivet 808 of second image 800. As depicted, outline 1206 and rivet 808 are irregular. Points 1208 correspond approximately to number of locations 1012 of rivet 808 of FIG. 8.

In this illustrative example, determining the rivet concentricity comprises determining distances 1306 between points 1208 of outline 1206 of rivet 808 and centerpoint 1304. In this illustrative example, the rivet concentricity is a smallest value of distances 1306.

Representative analysis 1302 includes distance 1308, distance 1310, and distance 1312. Although only three distances are depicted, any desirable number of distances may be determined. In this illustrative example, distance 1312 is the smallest value. In this illustrative example, distance 1312 is set as the rivet concentricity.

Figure 14:
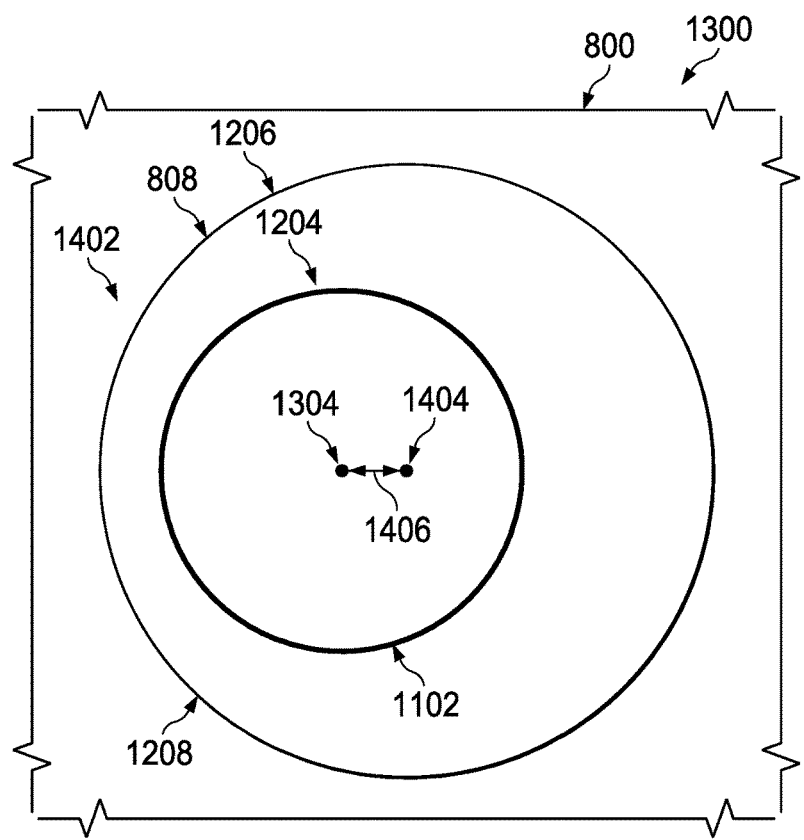
FIG. 14 is an illustration of representative analysis overlaid on a portion of a second image in accordance with an illustrative embodiment.

Turning now to FIG. 14, an illustration of representative analysis overlaid on a portion of a second image is depicted in accordance with an illustrative embodiment. View 1400 is a view of rivet 808 of second image 800 with representative analysis 1402. Representative analysis 1402 is a series of visual indicators of analysis performed by comparator 209 of FIG. 2.

As discussed above with reference to FIG. 9, an analysis is performed to determine number of locations 912 of hole 708. Number of locations 912 of hole 708 are a detected edge of hole 708.

As discussed above with reference to FIG. 10, an analysis is performed to determine number of locations 1012 of rivet 808. Number of locations 1012 of rivet 808 is a detected edge of the button of rivet 808.

Representative analysis 1402 includes outline 1102. Outline 1102 comprises points 1204 representative of hole 708 of first image 700. As depicted, outline 1102 is approximately circular. Points 1204 correspond approximately to number of locations 912 of hole 708 of FIG. 7. Centerpoint 1304 of outline 1102 of hole 708 of FIG. 7 is determined during the analysis.

Outline 1206 comprises points 1208 representative of rivet 808 of second image 800. As depicted, outline 1206 and rivet 808 are irregular. Points 1208 correspond approximately to number of locations 1012 of rivet 808 of FIG. 8. Mass centerpoint 1404 of outline 1206 of rivet 808 is determined during the analysis.

In this illustrative example, determining the rivet concentricity comprises determining distance 1406 between centerpoint 1304 and mass centerpoint 1404. In this illustrative example, the rivet concentricity is distance 1406.

FIGS. 12-14 are representation of analyses performed on a first image and a second image. Although the depictions of representative analysis 1202, representative analysis 1302 and representative analysis 1402 are illustrations and overlays, in some illustrative examples these analyses may instead be pictorially depicted. In some illustrative examples, at least some of the analyses may be calculations without graphic depictions.

FIGS. 12-14 are each images of rivet 808 of FIG. 8. In other illustrative examples, a button of a rivet may be a different shape, a different size, or a different location relative to a hole containing the rivet. For example, in each of FIGS. 12-14, rivet 808 completely covers hole 708 from view. In other illustrative examples, a rivet may not completely cover the associated hole. In these illustrative examples, at least one distance between a point of the outline of the rivet and a point of the outline of the hole is negative. In some illustrative examples, when the distance is negative, a respective rivet, such as rivet 808, will automatically be reworked.

Figure 15:
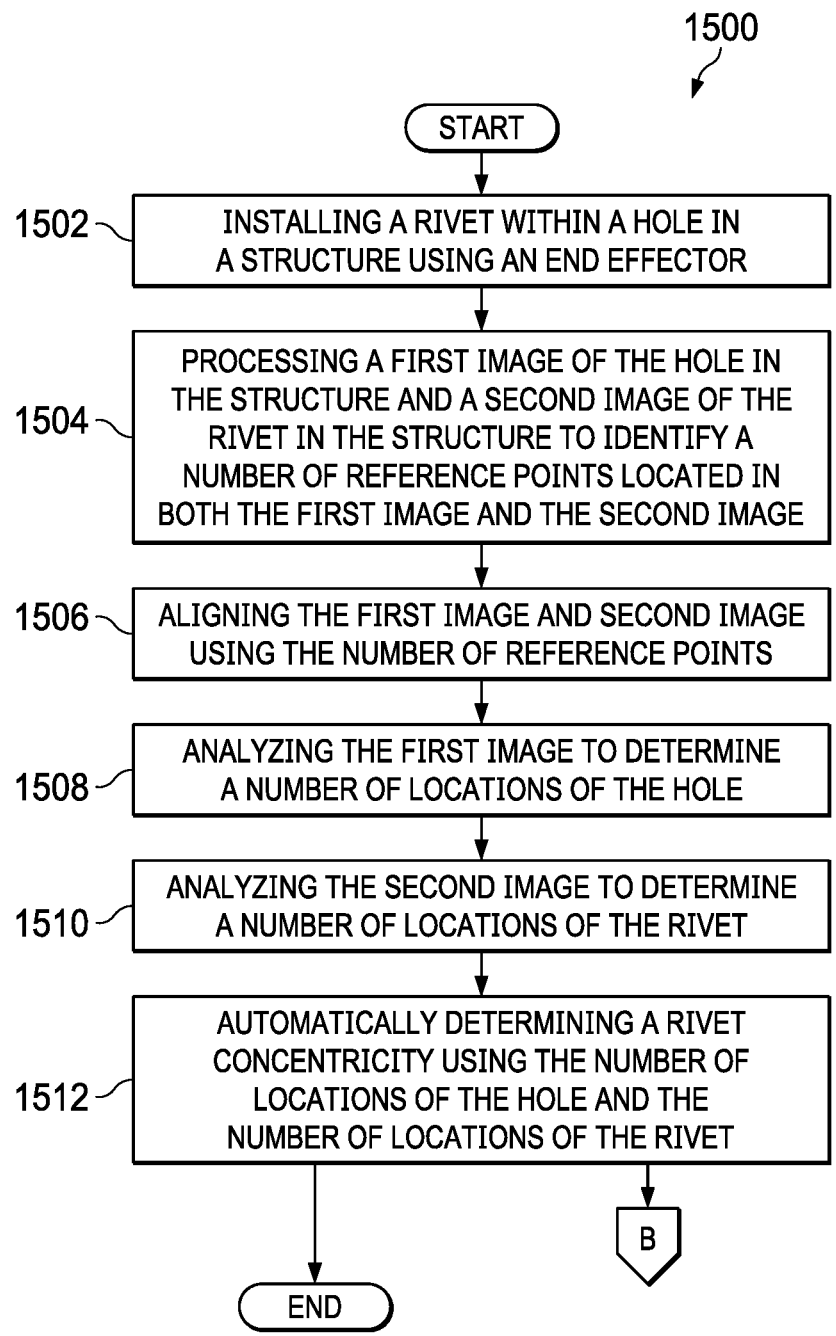
FIG. 15 is an illustration of a flowchart of a process for automated rivet measurement in accordance with an illustrative embodiment.

Turning now to FIG. 15, an illustration of a flowchart of a process for automated rivet measurement is depicted in accordance with an illustrative embodiment. Automated rivet measurement system 202 may perform method 1500 within manufacturing environment 200 of FIG. 2. Method 1500 may be performed in manufacturing environment 300 of FIG. 3 using automated rivet measurement system 308. Method 1500 may be performed on structure 304 of FIGS. 3-5. Method 1500 may be performed using first image 700 and second image 800 of FIGS. 7-11. Method 1500 installs a rivet within a hole in a structure using an end effector (operation 1502).

Method 1500 processes a first image of the hole in the structure and a second image of the rivet in the structure to identify a number of reference points located in both the first image and the second image (operation 1504). In some illustrative examples, the first image and the second image are taken in situ. For example, each of the first image and the second image may be taken during other manufacturing operations, such as drilling, riveting, or movement after drilling or riveting. When the first image and the second image are taken in situ, additional inspection steps are not created. When the first image and the second image are taken in situ, additional end effector movements may not be used. When the first image and the second image are taken in situ, inspection time may be reduced.

In some illustrative examples, first image and second image are taken using the same camera. For example, the first image and the second image may be taken using a camera attached to an end effector used to drill the hole and install the rivet. As another example, a first end effector is used to drill the hole and the first image and the second image may be taken using a camera attached to a second end effector used to install the rivet.

In other illustrative examples, first image and second image are taken using different cameras. For example, the first image may be taken using a camera attached to an end effector used to drill the hole while the second image is taken using a second camera attached to a second end effector used to install the rivet.

In some illustrative examples, small positioning movements are added to position the number of cameras to take first image and second image. In some illustrative examples, small additional positioning movements may be added between other manufacturing operations. In some illustrative examples, an end effector is stopped momentarily between manufacturing operations to take at least one of the first image or the second image.

Method 1500 aligns the first image and second image using the number of reference points (operation 1506). In some illustrative examples, the first image and the second image are oriented relative to a shared coordinate system. In some illustrative examples, coordinates of features of the first image and the second image are saved relative to a shared coordinate system. In some illustrative examples, the second image may be overlaid over the first image.

Method 1500 analyzes the first image to determine a number of locations of the hole (operation 1508). In some illustrative examples, the number of locations include locations of a boundary of the hole.

Method 1500 analyzes the second image to determine a number of locations of the rivet (operation 1510). In some illustrative examples, the number of locations include a boundary of the button of the rivet.

Method 1500 automatically determines a rivet concentricity using the number of locations of the hole and the number of locations of the rivet (operation 1512). Afterwards the method terminates.

In some illustrative examples, method 1500 determines the rivet concentricity in situ. When rivet concentricity is determined in situ, method 1500 may not increase manufacturing time. When rivet concentricity is determined in situ, method 1500 may not add end effector movements. In some illustrative examples, method 1500 determines the rivet concentricity during at least one of drilling, installing rivets, or movements after drilling or installing rivets.

Figure 16:
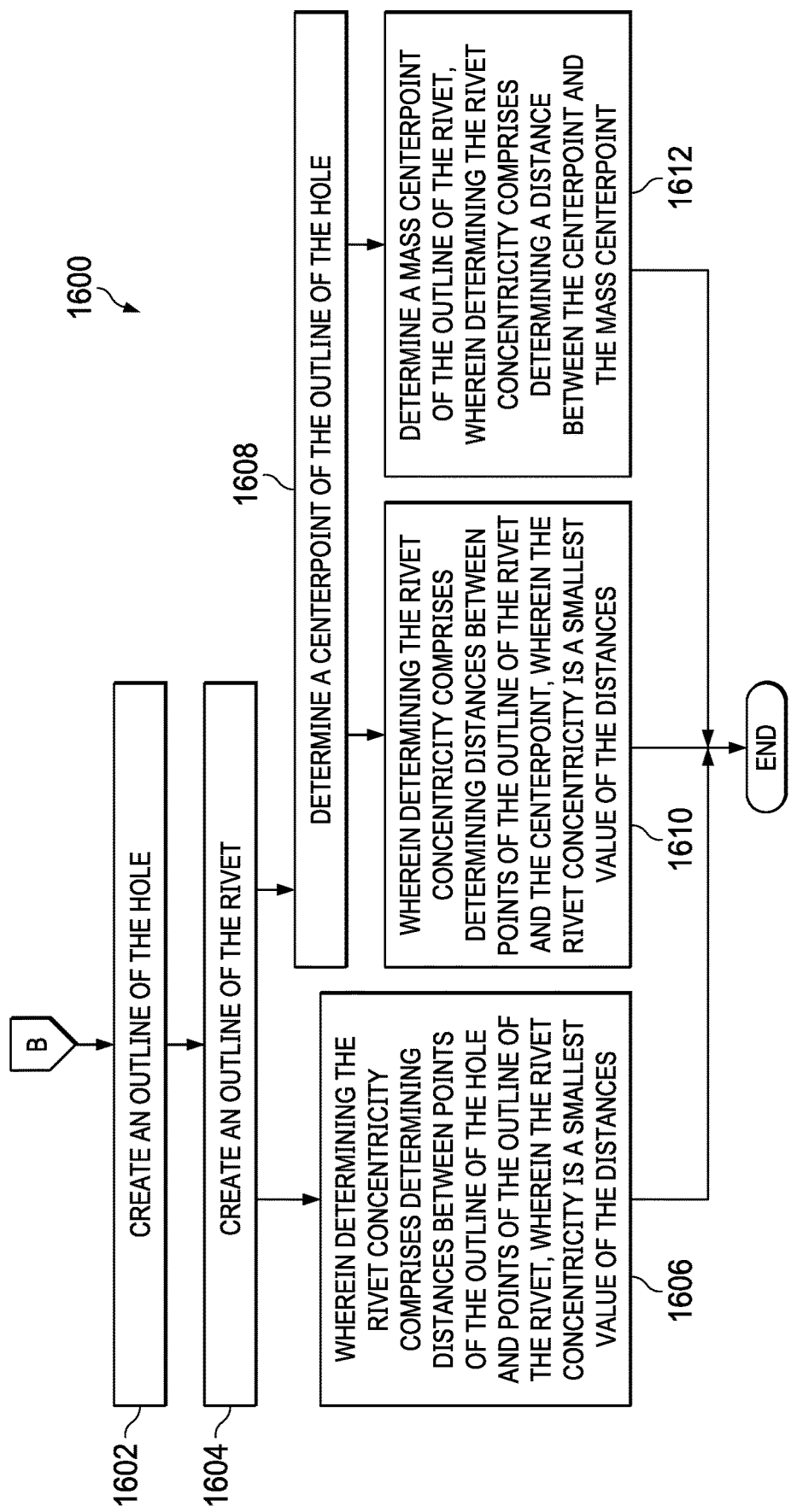
FIG. 16 is an illustration of a flowchart of analysis options in accordance with an illustrative embodiment.

Turning now to FIG. 16, an illustration of a flowchart of analysis options is depicted in accordance with an illustrative embodiment. Method 1600 presents analysis options that may be implemented as part of method 1500 or method 1700.

Method 1600 creates an outline of the hole (operation 1602). Method 1600 creates an outline of the rivet (operation 1604). In some illustrative examples, determining the rivet concentricity comprises determining distances between points of the outline of the hole and points of the outline of the rivet, wherein the rivet concentricity is a smallest value of the distances (operation 1606).

In some illustrative examples, method determines a centerpoint of the outline of the hole (operation 1608). In some illustrative examples, determining the rivet concentricity comprises determining distances between points of the outline of the rivet and the centerpoint, wherein the rivet concentricity is a smallest value of the distance (operation 1610). In some illustrative examples, method determines a mass centerpoint of the outline of the rivet, wherein determining the rivet concentricity comprises determining a distance between the centerpoint and the mass centerpoint (operation 1612). After any of operation 1606, operation 1610, or operation 1612, method 1600 terminates.

Figure 17:
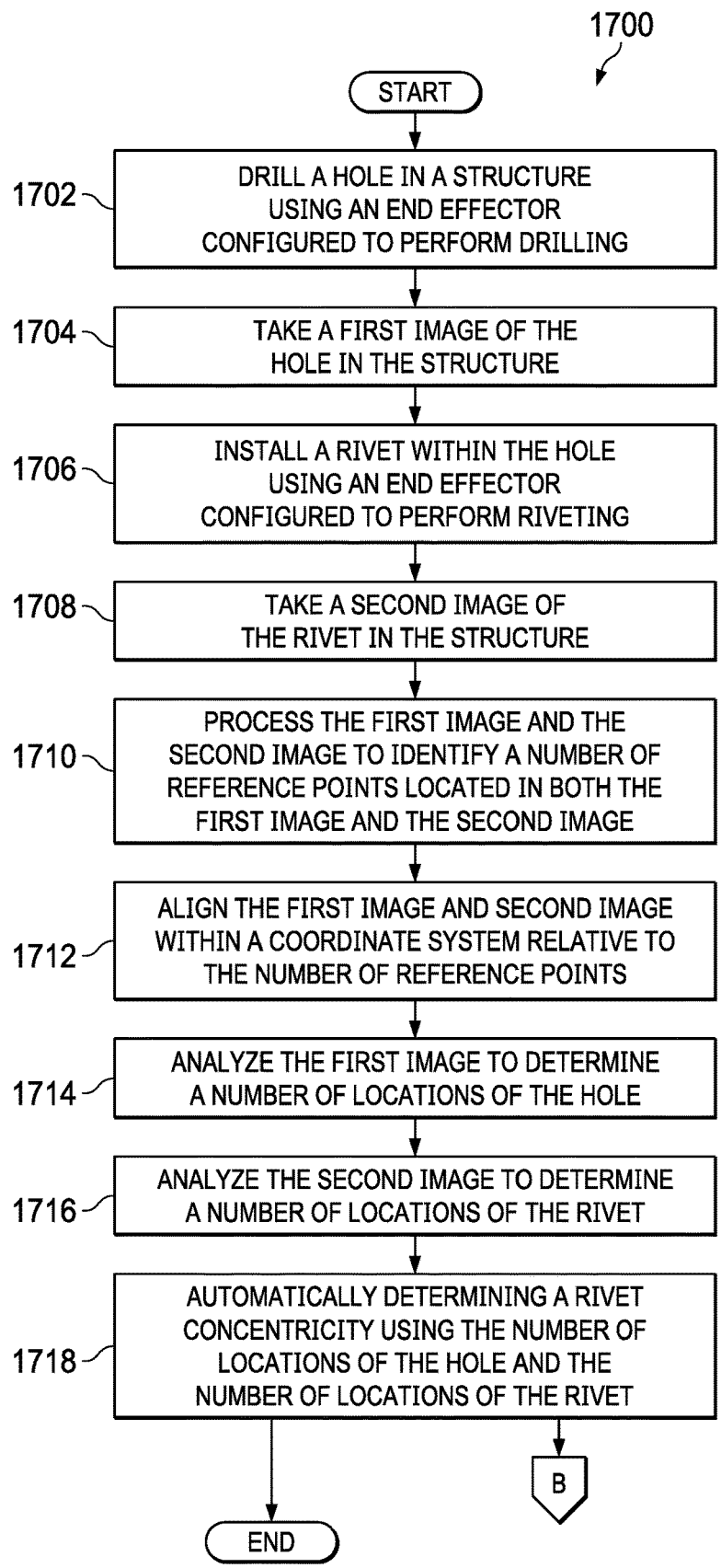
FIG. 17 is an illustration of a flowchart of a process for automated rivet measurement in accordance with an illustrative embodiment.

Turning now to FIG. 17, an illustration of a flowchart of a process for automated rivet measurement is depicted in accordance with an illustrative embodiment. Automated rivet measurement system 202 may perform method 1700 within manufacturing environment 200 of FIG. 2. Method 1700 may be performed in manufacturing environment 300 of FIG. 3 using automated rivet measurement system 308. Method 1700 may be performed on structure 304 of FIGS. 3-5. Method 1700 may be performed using first image 700 and second image 800 of FIGS. 7-11.

Method 1700 drills a hole in a structure using an end effector configured to perform drilling (operation 1702). The hole in the structure is drilled using a first end effector. Method 1700 takes a first image of the hole in the structure (operation 1704). In some illustrative examples, the first image is taken using a camera attached to the first end effector. In some illustrative examples, the first image is taken in situ. For example, the first image may be taken during other manufacturing operations, such as drilling, riveting, or movement after drilling or riveting. When the first image is taken in situ, additional inspection steps are not created. When the first image is taken in situ, additional end effector movements may not be used. When the first image is taken in situ, inspection time may be reduced.

Method 1700 installs a rivet within the hole using an end effector configured to perform riveting (operation 1706). The rivet is installed using an end effector. In some illustrative examples, the rivet is installed using the first end effector used to drill the hole. In other illustrative examples, the rivet is installed with a second end effector. Method 1700 takes a second image of the rivet in the structure (operation 1708).

In some illustrative examples, first image and second image are taken using the same camera. In these illustrative examples, taking the first image and taking the second image are performed by a same camera. For example, the first image and the second image may be taken using a camera attached to the first end effector used to drill the hole and install the rivet. As another example, the first end effector is used to drill the hole and the first image and the second image may be taken using a camera attached to the second end effector used to install the rivet. In some illustrative examples, at least one of taking the first image or taking the second image is performed by a camera attached to the end effector configured to perform drilling. In some illustrative examples, at least one of taking the first image or taking the second image is performed by a camera attached to the end effector configured to perform riveting.

In other illustrative examples, first image and second image are taken using different cameras. For example, the first image may be taken using a camera attached to the first end effector used to drill the hole while the second image is taken using a second camera attached to the second end effector used to install the rivet.

In some illustrative examples, taking the first image and taking the second image are performed in situ. In some illustrative examples, small positioning movements are added to position the number of cameras to take first image and second image. In some illustrative examples, small additional positioning movements may be added between other manufacturing operations. In some illustrative examples, an end effector is stopped momentarily between manufacturing operations to take at least one of the first image or the second image. In some illustrative examples, taking the first image and taking the second image do not add movement steps to the end effector configured to perform drilling or the end effector configured to perform riveting.

Method 1700 processes the first image and the second image to identify a number of reference points located in both the first image and the second image (operation 1710). In some illustrative examples, method 1700 processes each of the first image and the second image automatically upon receipt. In some illustrative examples, method 1700 processes the first image and the second image after receiving both the first image and the second image.

Method 1700 aligns the first image and second image within a coordinate system relative to the number of reference points (operation 1712). Method 1700 analyzes the first image to determine a number of locations of the hole (operation 1714).

Method 1700 analyzes the second image to determine a number of locations of the rivet (operation 1716). Method 1700 automatically determines a rivet concentricity using the number of locations of the hole and the number of locations of the rivet (operation 1718). Afterwards the method terminates.

In some illustrative examples, method 1700 determines the rivet concentricity in situ. When rivet concentricity is determined in situ, method 1700 may not increase manufacturing time. When rivet concentricity is determined in situ, method 1700 may not add end effector movements. In some illustrative examples, method 1700 determines the rivet concentricity during at least one of drilling, installing rivets, or movements after drilling or installing rivets.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent at least one of a module, a segment, a function, or a portion of an operation or step. For example, one or more of the blocks may be implemented as program code, hardware, or a combination of the program code and hardware. When implemented in hardware, the hardware may, for example, take the form of integrated circuits that are manufactured or configured to perform one or more operations in the flowcharts or block diagrams. When implemented as a combination of program code and hardware, the implementation may take the form of firmware. Each block in the flowcharts or the block diagrams may be implemented using special purpose hardware systems that perform the different operations or combinations of special purpose hardware and program code run by the special purpose hardware.

In some alternative implementations of an illustrative embodiment, the function or functions noted in the blocks may occur out of the order noted in the figures. For example, in some cases, two blocks shown in succession may be performed substantially concurrently, or the blocks may sometimes be performed in the reverse order, depending upon the functionality involved. Also, other blocks may be added, in addition to the illustrated blocks, in a flowchart or block diagram.

In some examples, in method 1500, identifying the number of reference points located in both the first image and the second image comprises identifying a rivet present in the first image and the second image as a first feature of the number of reference points. In some examples, in method 1500, identifying the number of reference points located in both the first image and the second image comprises identifying another rivet present in the first image and the second image as a second feature of the number of reference points. In some examples, in method 1500, the number of reference points comprises at least one of a rivet, a hole, or an edge of the structure.

Figure 18:
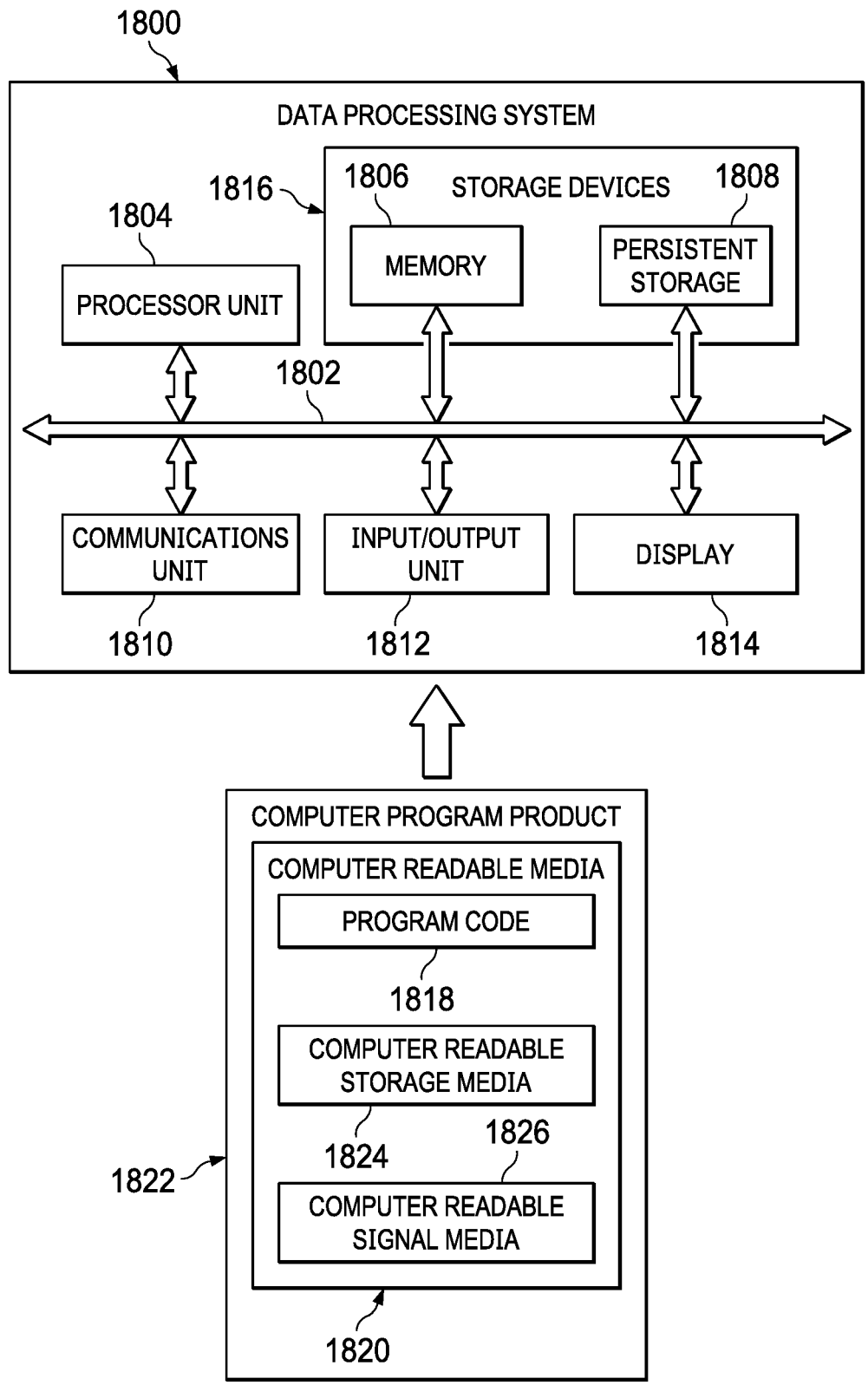
FIG. 18 is an illustration of a block diagram of a data processing system in accordance with an illustrative embodiment.

Turning now to FIG. 18, an illustration of a block diagram of a data processing system is depicted in accordance with an illustrative embodiment. Data processing system 1800 may be used to implement computer system 232 in FIG. 2. In this illustrative example, data processing system 1800 includes communications framework 1802, which provides communications between processor unit 1804, memory 1806, persistent storage 1808, communications unit 1810, input/output unit 1812, and display 1814. In this example, communications framework 1802 may take the form of a bus system.

Processor unit 1804 serves to execute instructions for software that may be loaded into memory 1806. Processor unit 1804 may be a number of processors, a multi-processor core, or some other type of processor, depending on the particular implementation.

Memory 1806 and persistent storage 1808 are examples of storage devices 1816. A storage device is any piece of hardware that is capable of storing information, such as, for example, without limitation, at least one of data, program code in functional form, or other suitable information either on a temporary basis, a permanent basis, or both on a temporary basis and a permanent basis. Storage devices 1816 may also be referred to as computer readable storage devices in these illustrative examples. Memory 1806, in these examples, may be, for example, a random-access memory or any other suitable volatile or non-volatile storage device. Persistent storage 1808 may take various forms, depending on the particular implementation.

For example, persistent storage 1808 may contain one or more components or devices. For example, persistent storage 1808 may be a hard drive, a solid state hard drive, a flash memory, a rewritable optical disk, a rewritable magnetic tape, or some combination of the above. The media used by persistent storage 1808 also may be removable. For example, a removable hard drive may be used for persistent storage 1808.

Communications unit 1810, in these illustrative examples, provides for communications with other data processing systems or devices. In these illustrative examples, communications unit 1810 is a network interface card.

Input/output unit 1812 allows for input and output of data with other devices that may be connected to data processing system 1800. For example, input/output unit 1812 may provide a connection for user input through at least one of a keyboard, a mouse, or some other suitable input device. Further, input/output unit 1812 may send output to a printer. Display 1814 provides a mechanism to display information to a user.

Instructions for at least one of the operating system, applications, or programs may be located in storage devices 1816, which are in communication with processor unit 1804 through communications framework 1802. The processes of the different embodiments may be performed by processor unit 1804 using computer implemented instructions, which may be located in a memory, such as memory 1806.

These instructions are referred to as program code, computer usable program code, or computer readable program code that may be read and executed by a processor in processor unit 1804. The program code in the different embodiments may be embodied on different physical or computer readable storage media, such as memory 1806 or persistent storage 1808.

Program code 1818 is located in a functional form on computer readable media 1820 that is selectively removable and may be loaded onto or transferred to data processing system 1800 for execution by processor unit 1804. Program code 1818 and computer readable media 1820 form computer program product 1822 in these illustrative examples. In one example, computer readable media 1820 may be computer readable storage media 1824 or computer readable signal media 1826.

In these illustrative examples, computer readable storage media 1824 is a physical or tangible storage device used to store program code 1818 rather than a medium that propagates or transmits program code 1818.

Alternatively, program code 1818 may be transferred to data processing system 1800 using computer readable signal media 1826. Computer readable signal media 1826 may be, for example, a propagated data signal containing program code 1818. For example, computer readable signal media 1826 may be at least one of an electromagnetic signal, an optical signal, or any other suitable type of signal. These signals may be transmitted over at least one of communications links, such as wireless communications links, optical fiber cable, coaxial cable, a wire, or any other suitable type of communications link.

The different components illustrated for data processing system 1800 are not meant to provide architectural limitations to the manner in which different embodiments may be implemented. The different illustrative embodiments may be implemented in a data processing system including components, in addition to or in place of those illustrated, for data processing system 1800. Other components shown in FIG. 18 can be varied from the illustrative examples shown. The different embodiments may be implemented using any hardware device or system capable of running program code 1818.

Figure 19:
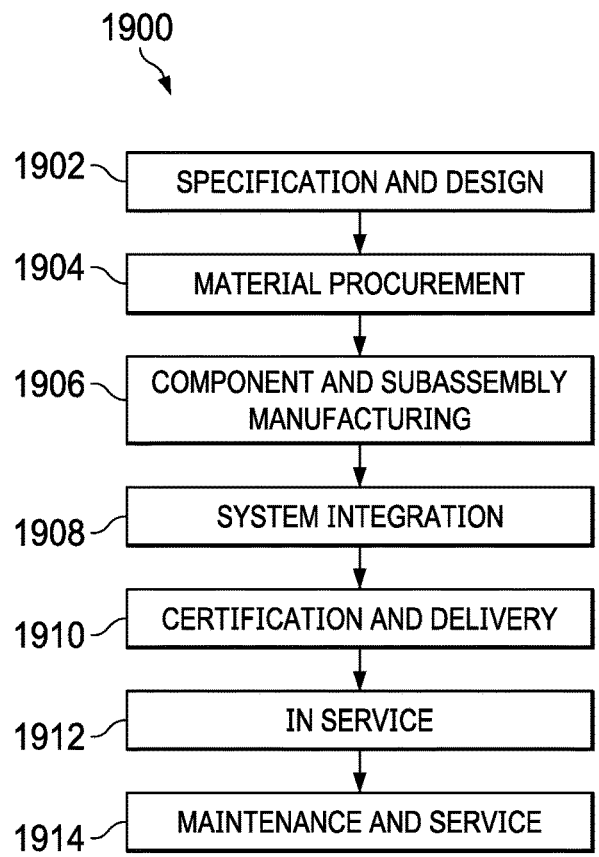
FIG. 19 is an illustration of a block diagram of an aircraft manufacturing and service method in accordance with an illustrative embodiment.
Figure 20:
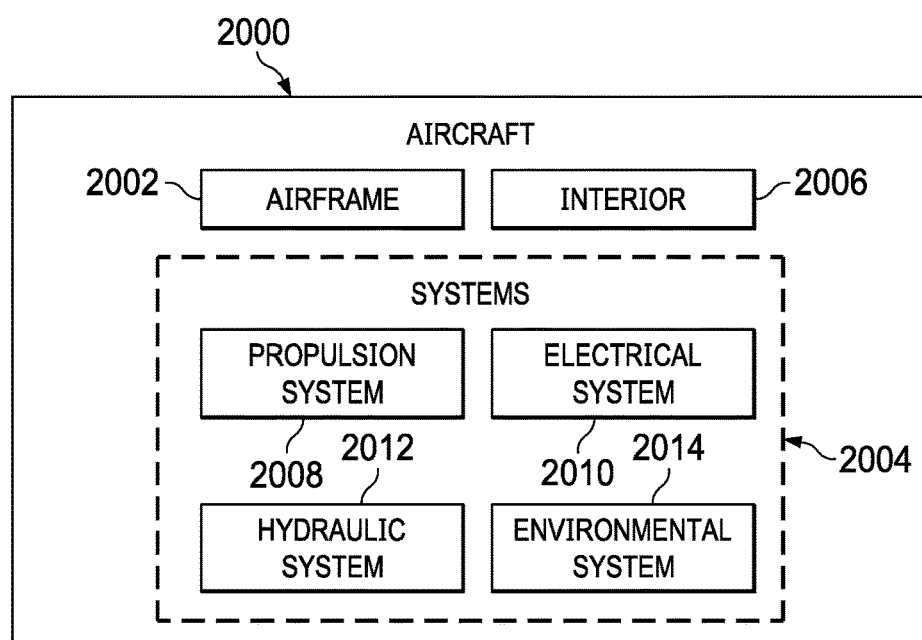
FIG. 20 is an illustration of a block diagram of an aircraft in which an illustrative embodiment may be implemented.

The illustrative embodiments of the present disclosure may be described in the context of aircraft manufacturing and service method 1900 as shown in FIG. 19 and aircraft 2000 as shown in FIG. 20. Turning first to FIG. 19, an illustration of a block diagram of an aircraft manufacturing and service method is depicted in accordance with an illustrative embodiment. During pre-production, aircraft manufacturing and service method 1900 may include specification and design 1902 of aircraft 2000 in FIG. 20 and material procurement 1904.

During production, component and subassembly manufacturing 1906 and system integration 1908 of aircraft 2000 in FIG. 20 takes place. Thereafter, aircraft 2000 in FIG. 20 may go through certification and delivery 1910 in order to be placed in service 1912. While in service 1912 by a customer, aircraft 2000 in FIG. 20 is scheduled for routine maintenance and service 1914, which may include modification, reconfiguration, refurbishment, or other maintenance and service.

Each of the processes of aircraft manufacturing and service method 1900 may be performed or carried out by a system integrator, a third party, an operator, or some combination thereof. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 20, an illustration of a block diagram of an aircraft is depicted in which an illustrative embodiment may be implemented. In this example, aircraft 2000 is produced by aircraft manufacturing and service method 1900 in FIG. 19 and may include airframe 2002 with plurality of systems 2004 and interior 2006. Examples of systems 2004 include one or more of propulsion system 2008, electrical system 2010, hydraulic system 2012, and environmental system 2014. Any number of other systems may be included. Although an aerospace example is shown, different illustrative embodiments may be applied to other industries, such as the automotive industry.

The apparatuses and methods embodied herein may be employed during at least one of the stages of aircraft manufacturing and service method 1900 in FIG. 19. In one illustrative example, components or subassemblies produced in component and subassembly manufacturing 1906 in FIG. 19 may be fabricated or manufactured in a manner similar to components or subassemblies produced while aircraft 2000 is in service 1912 in FIG. 19. As yet another example, one or more apparatus embodiments, method embodiments, or a combination thereof may be utilized during production stages, such as component and subassembly manufacturing 1906 and system integration 1908 in FIG. 19. One or more apparatus embodiments, method embodiments, or a combination thereof may be utilized while aircraft 2000 is in service 1912, during maintenance and service 1914 in FIG. 19, or both. For example, inspection of rivets, such as rivets 203, may be performed using an automated rivet measurement system during component and subassembly manufacturing 1906 to inspect the rivets. Additionally, the automated rivet measurement system, such as automated rivet measurement system 202 of FIG. 2, also may be used during maintenance and service 1914 to inspect already installed rivets, rivets installed during routine maintenance including reconfiguration, refurbishment, and other maintenance or service.

One or more apparatus embodiments, method embodiments, or a combination thereof may be utilized in any desirable components of aircraft 2000. For example, inspection of rivets, such as rivets 203 of FIG. 2, may be performed using an automated rivet measurement system during installation of rivets in airframe 2002. As another example, inspection of rivets, such as rivets 203, may be performed using an automated rivet measurement system during installation of rivets in interior 2006.

The use of a number of the different illustrative embodiments may substantially expedite the assembly of aircraft 2000, reduce the cost of aircraft 2000, or both expedite the assembly of aircraft 2000 and reduce the cost of aircraft 2000. For example, the use of an automated rivet measurement system, in accordance with an illustrative example, may reduce the time and cost for manufacturing aircraft 2000. For example, the time needed to inspect rivets may be reduced. In this manner, aircraft 2000 may be manufactured more quickly as compared to using current techniques that involve destructive testing measurements.

Thus, one or more technical solutions are present that overcome a technical problem with obtaining measurements of rivet concentricity without using destructive testing. One or more technical solutions may provide a technical effect identifying rivet concentricity without having to perform destructive testing. Also, one or more technical solutions are present that provide an ability to determine a rivet concentricity in situ.

The description of the different illustrative embodiments has been presented for purposes of illustration and description and is not intended to be exhaustive or limited to the embodiments in the form disclosed. The different illustrative examples describe components that perform actions or operations. In an illustrative embodiment, a component may be configured to perform the action or operation described. For example, the component may have a configuration or design for a structure that provides the component an ability to perform the action or operation that is described in the illustrative examples as being performed by the component.

Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for automated non-destructive testing of rivet concentricity, the method comprising:
   installing a rivet within a hole in a structure using an end effector;
   processing a first image of the hole in the structure and a second image of the rivet in the structure to identify a number of reference points located in both the first image and the second image;
   aligning the first image and second image using the number of reference points;
   analyzing the first image to determine a number of locations of the hole;
   analyzing the second image to determine a number of locations of the rivet;
   automatically determining a rivet concentricity using the number of locations of the hole and the number of locations of the rivet;
   creating an outline of the hole;
   determining a centerpoint of the outline of the hole;
   creating an outline of the rivet; and
   determining a mass centerpoint of the outline of the rivet, wherein determining the rivet concentricity comprises determining a distance between the centerpoint and the mass centerpoint.

2. The method of claim 1
   wherein determining the rivet concentricity comprises determining distances between points of the outline of the hole and points of the outline of the rivet, wherein the rivet concentricity is a smallest value of the distances.

3. The method of claim 1 wherein determining the rivet concentricity comprises determining distances between points of the outline of the rivet and the centerpoint, wherein the rivet concentricity is a smallest value of the distances.

4. The method of claim 1, wherein identifying the number of reference points located in both the first image and the second image comprises identifying a rivet present in the first image and the second image as a first feature of the number of reference points.

5. The method of claim 4, wherein identifying the number of reference points located in both the first image and the second image comprises identifying another rivet present in the first image and the second image as a second feature of the number of reference points.

6. The method of claim 1, wherein the number of reference points comprises at least one of a rivet, a hole, or an edge of the structure.

7. An automated rivet measurement system comprising:
    a number of end effectors configured to perform drilling and riveting on a structure;
    a number of cameras connected to the number of end effectors, the number of cameras configured to take a first image of a hole in the structure and a second image of a rivet in the hole;
    a processor configured to process the first image and the second image to identify a number of reference points in the first image and the second image; and
    a comparator configured to determine a rivet concentricity using the hole in the first image and the rivet in the second image, in which the first image and the second image are aligned using the number of reference points;
    wherein the comparator is configured to create an outline of the hole and create an outline of the rivet, wherein determining the rivet concentricity comprises determining distances between points of the outline of the hole and points of the outline of the rivet, wherein the rivet concentricity is a smallest value of the distances.

8. The automated rivet measurement system of claim 7, wherein the comparator is further configured to analyze the first image to determine a number of locations of the hole, analyze the second image to determine a number of locations of the rivet, and determine a rivet concentricity using the number of locations of the hole and the number of locations of the rivet.

9. The automated rivet measurement system of claim 7, wherein the comparator is configured to determine a centerpoint of the outline of the hole, wherein determining the rivet concentricity comprises determining distances between points of the outline of the rivet and the centerpoint, wherein the rivet concentricity is a smallest value of the distances.

10. The automated rivet measurement system of claim 7, wherein the comparator is configured to determine a centerpoint of the outline of the hole, and determine a mass centerpoint of the outline of the rivet, wherein determining the rivet concentricity comprises determining a distance between the centerpoint and the mass centerpoint.

11. The automated rivet measurement system of claim 7, wherein the number of end effectors comprises one end effector to perform both the drilling and the riveting.

12. The automated rivet measurement system of claim 7, wherein the number of end effectors comprises a first end effector to perform drilling and a second end effector to perform the riveting, and wherein the number of cameras comprises a camera connected to the first end effector configured to take the first image and a second camera connected to the second end effector configured to take the second image.

13. The automated rivet measurement system of claim 7, wherein the first image and the second image are both taken in situ.

14. The automated rivet measurement system of claim 7, wherein the first image and the second image are both taken by a same camera of the number of cameras.

15. A method for automated non-destructive testing of rivet concentricity, the method comprising:
    drilling a hole in a structure using an end effector configured to perform drilling;
    taking a first image of the hole in the structure;
    installing a rivet within the hole using an end effector configured to perform riveting;
    taking a second image of the rivet in the structure;
    processing the first image and the second image to identify a number of reference points located in both the first image and the second image;
    aligning the first image and second image within a coordinate system relative to the number of reference points;
    analyzing the first image to determine a number of locations of the hole;
    analyzing the second image to determine a number of locations of the rivet;
    automatically determining a rivet concentricity using the number of locations of the hole and the number of locations of the rivet;
    creating an outline of the hole;
    determining a centerpoint of the outline of the hole; and
    creating an outline of the rivet, wherein determining the rivet concentricity comprises determining distances between points of the outline of the rivet and the centerpoint, wherein the rivet concentricity is a smallest value of the distances.

16. The method of claim 15 wherein determining the rivet concentricity comprises determining distances between points of the outline of the hole and points of the outline of the rivet, wherein the rivet concentricity is a smallest value of the distances.

17. The method of claim 15 further comprising:
    determining a mass centerpoint of the outline of the rivet, wherein determining the rivet concentricity comprises determining a distance between the centerpoint and the mass centerpoint.

18. The method of claim 15, wherein identifying the number of reference points located in both the first image and the second image comprises identifying a rivet present in the first image and the second image as a first feature of the number of reference points.

19. The method of claim 18, wherein identifying the number of reference points located in both the first image and the second image comprises identifying another rivet present in the first image and the second image as a second feature of the number of reference points.

20. The method of claim 15, wherein taking the first image and taking the second image are performed in situ.

21. The method of claim 15, wherein taking the first image and taking the second image are performed by a same camera.

22. The method of claim 15, wherein at least one of taking the first image or taking the second image is performed by a camera attached to the end effector configured to perform drilling.

23. The method of claim 15, wherein at least one of taking the first image or taking the second image is performed by a camera attached to the end effector configured to perform riveting.

24. The method of claim 15, wherein taking the first image and taking the second image do not add movement steps to the end effector configured to perform drilling or the end effector configured to perform riveting.

25. A method for automated non-destructive testing of rivet concentricity, the method comprising:
- installing a rivet within a hole in a structure using an end effector;
- processing a first image of the hole in the structure and a second image of the rivet in the structure to identify a number of reference points located in both the first image and the second image;
- aligning the first image and second image using the number of reference points;
- analyzing the first image to determine a number of locations of the hole;
- analyzing the second image to determine a number of locations of the rivet;
- automatically determining a rivet concentricity using the number of locations of the hole and the number of locations of the rivet;
- creating an outline of the hole; and
- creating an outline of the rivet, wherein determining the rivet concentricity comprises determining distances between points of the outline of the hole and points of the outline of the rivet, wherein the rivet concentricity is a smallest value of the distances.

* * * * *